US012644046B2

(12) United States Patent
Suruga et al.

(10) Patent No.: US 12,644,046 B2
(45) Date of Patent: Jun. 2, 2026

(54) ORGANIC ELECTROLUMINESCENT DEVICE

(71) Applicants: Hodogaya Chemical Co., Ltd., Tokyo (JP); SFC Co., Ltd., Cheongju-si (KR)

(72) Inventors: Kazuyuki Suruga, Tokyo (JP); Kouki Kase, Tokyo (JP); Takeshi Yamamoto, Tokyo (JP); Shuichi Hayashi, Tokyo (JP); Soon-wook Cha, Cheongju-si (KR); Sung-hoon Joo, Cheongju-si (KR); Byung-sun Yang, Cheongju-si (KR); Ji-Hwan Kim, Cheongju-si (KR)

(73) Assignees: Hodogaya Chemical Co., Ltd., Tokyo (JP); SFC Co., Ltd., Cheongju-si (KR)

( * ) Notice: Subject to any disclaimer, the term of this patent is extended or adjusted under 35 U.S.C. 154(b) by 1056 days.

(21) Appl. No.: 17/770,392

(22) PCT Filed: Oct. 20, 2020

(86) PCT No.: PCT/JP2020/039313

§ 371 (c)(1),
(2) Date: Apr. 20, 2022

(87) PCT Pub. No.: WO2021/079856

PCT Pub. Date: Apr. 29, 2021

(65) Prior Publication Data

US 2022/0416165 A1 Dec. 29, 2022

(30) Foreign Application Priority Data

Oct. 23, 2019 (JP) ................................ 2019-192483

(51) Int. Cl.

| | |
|---|---|
| ***H01L 51/54*** | (2006.01) |
| ***C07C 211/54*** | (2006.01) |
| ***C07C 211/58*** | (2006.01) |
| ***C07F 5/02*** | (2006.01) |
| ***C09K 11/06*** | (2006.01) |
| ***H10K 85/60*** | (2023.01) |
| *H10K 50/15* | (2023.01) |

(52) U.S. Cl.

CPC ............ *C09K 11/06* (2013.01); *C07C 211/54* (2013.01); *C07C 211/58* (2013.01); *C07F 5/027* (2013.01); *H10K 85/633* (2023.02); *H10K 85/658* (2023.02); *C07C 2603/26* (2017.05); *C09K 2211/1007* (2013.01); *C09K 2211/1011* (2013.01); *C09K 2211/1014* (2013.01); *C09K 2211/1018* (2013.01); *H10K 50/15* (2023.02); *H10K 50/156* (2023.02); *H10K 85/615* (2023.02); *H10K 85/626* (2023.02)

(58) Field of Classification Search

None

See application file for complete search history.

(56) References Cited

U.S. PATENT DOCUMENTS

| | | | | |
|---|---|---|---|---|
| 10,566,540 | B2 | 2/2020 | Hayashi et al. | |
| 10,923,663 | B2 | 2/2021 | Takada et al. | |
| 10,981,938 | B2 | 4/2021 | Joo et al. | |
| 2010/0155714 | A1 | 6/2010 | Seo et al. | |
| 2015/0236274 | A1* | 8/2015 | Hatakeyama ........ | H10K 85/631 548/405 |
| 2018/0026199 | A1* | 1/2018 | Hayashi ............... | C07D 471/04 257/40 |
| 2018/0114907 | A1 | 4/2018 | Takada et al. | |
| 2020/0106017 | A1 | 4/2020 | Ha et al. | |
| 2020/0172558 | A1 | 6/2020 | Joo et al. | |
| 2020/0194673 | A1 | 6/2020 | Ha et al. | |
| 2021/0135110 | A1 | 5/2021 | Takada et al. | |
| 2022/0029101 | A1 | 1/2022 | Lee et al. | |
| 2022/0102635 | A1 | 3/2022 | Joo et al. | |

FOREIGN PATENT DOCUMENTS

| | | | |
|---|---|---|---|
| CN | 106866498 | A | 6/2017 |
| JP | 2004 -204238 | A | 7/2004 |
| JP | 2018-065806 | A | 4/2018 |
| JP | 2020-083896 | A | 6/2020 |
| JP | 2020-136675 | A | 8/2020 |
| KR | 10-2019-0053768 | A | 5/2019 |
| KR | 20190069224 | A | 6/2019 |
| KR | 10-2019-0078482 | A | 7/2019 |
| KR | 10-2020-0077860 | A | 7/2020 |
| KR | 10-2020-0088235 | A | 7/2020 |
| WO | 2016125706 | A1 | 8/2016 |

OTHER PUBLICATIONS

Office Action mailed Jun. 11, 2024, issued for JP2021-553438 and English translation thereof.

Supplementary European Search Report dated Oct. 13, 2023, issued for the corresponding European Patent Application No. 20878630.1.

Office Action mailed Mar. 7, 2025, issued for the corresponding Chinese Patent Application No. 202080073485.0.

* cited by examiner

*Primary Examiner* — Andrew K Bohaty

(74) *Attorney, Agent, or Firm* — Troutman Pepper Locke LLP; James E. Armstrong, IV

(57) ABSTRACT

The present inventors have focused the fact that an arylamine material having a specific structure is excellent in hole injection/transport ability, thin film stability and durability. The arylamine compound of the above can be selected as a material for the hole transport layer, holes injected from the anode side can be efficiently transported. Furthermore, various organic EL devices combining electron transport materials having a specific structure and the like were manufactured, and the characteristics of the devices were evaluated diligently.

13 Claims, 9 Drawing Sheets

(1-1)

(1-2)

(1-3)

(1-4)

(1-5)

(1-6)

(1-7)

(1-8)

(1-9)

(1-10)

(1-11)

(1-12)

(1-13)

(1-14)

(1-15)

(1-16)

(1-17)

(1-18)

(1-19)

(1-20)

(1-21)

(1-22)

(1-23)

(1-24)

(1-25)

(1-26)

(1-27)

(1-28)

(1-29)

(1-30)

(1-31)

(1-32)

(1-33)

(1-34)

(1-35)

(1-36)

(1-37)

(1-38)

(1-39)

(1-40)

(1-41)

(1-42)

(1－43)

(1－44)

(1－45)

(1－46)

(1－47)

(1－48)

(1－49)

(1－50)

(1－51)

(1－52)

(1－53)

(1－54)

(1－55)

(1-56)

(1-57)

(1-58)

(1-59)

(1-60)

(1-61)

(1-62)

(1-63)

(1-64)

(2－1)

(2－2)

(2－3)

(2－4)

(2－5)

(2－6)

(2－7)

(2－8)

(2－9)

(2－10)

(2－11)

(2－12)

(2－13)

(2－14)

(2－15)

(2－16)

(2－17)

(2－18)

(2－19)

(2－20)

(2－21)

(2－22)

(3-1)

(3-2)

(3-3)

(3-4)

(3-5)

(3-6)

(3-7)

(3-8)

ORGANIC ELECTROLUMINESCENT DEVICE

TECHNICAL FIELD

The present invention relates to an organic electroluminescent device which is a preferred self-luminous device for various display devices. Specifically, this invention relates to organic electroluminescent devices (hereinafter referred to as organic EL devices) using specific arylamine compounds.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/$m^2$ or more at a voltage of 10 V or less (refer to Patent Documents 1 and 2, for example).

To date, various improvements have been made for practical applications of the organic EL device. Various roles of the laminated structure are further subdivided to provide an EL device that includes an anode, a hole injection layer, a hole transport layer, a light emitting layer, an electron transport layer, an electron injection layer, and a cathode successively formed on a substrate, and high efficiency and durability have been achieved by the EL device (refer to Non-Patent Document 1, for example).

Further, there have been attempts to use triplet excitons for further improvements of luminous efficiency, and the use of a phosphorescence-emitting compound has been examined (refer to Non-Patent Document 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to Non-Patent Document 3, for example).

The light emitting layer can be also fabricated by doping a charge-transporting compound generally called a host material, with a fluorescent compound, a phosphorescence-emitting compound, or a delayed fluorescent-emitting material. As described in the Non-Patent Document, the selection of organic materials in an organic EL device greatly influences various device characteristics such as efficiency and durability (refer to Non-Patent Documents 1 to 3, for example).

In an organic EL device, charges injected from both electrodes recombine in a light emitting layer to cause emission. What is important here is how efficiently the hole and electron charges are transferred to the light emitting layer in order to form a device having excellent carrier balance. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di($\alpha$-naphthyl)benzidine (NPD) and various aromatic amine derivatives are known as the hole transport materials used for the organic EL device (refer to Patent Documents 1 and 2, for example). Although NPD has desirable hole transportability, its glass transition point (Tg), which is an index of heat resistance, is as low as 96° C., which causes the degradation of device characteristics by crystallization under a high-temperature condition (refer to Non-Patent Document 4, for example). The aromatic amine derivatives described in the Patent Documents include a compound known to have an excellent hole mobility of $10^{-3}$ $cm^2/Vs$ or higher (refer to Patent Documents 1 and 2, for example). However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency. Although an aromatic amine derivative having high durability is reported (refer to Patent Document 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as heat resistance and hole injectability (refer to Patent Documents 4 and 5, for example). However, while the devices using these compounds for the hole injection layer or the hole transport layer have been improved in heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport performances, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport performances, stability as a thin film and durability.

CITATION LIST

Patent Documents

Patent Document 1: JP-A-Hei-8-048656

Patent Document 2: Japanese Patent No. 3194657

Patent Document 3: Japanese Patent No. 4943840
Patent Document 4: JP-A-2006-151979
Patent Document 5: WO2008/062636
Patent Document 6: WO2014/009310

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: Appl. Phys. Let., 98, 083302 (2011)
Non-Patent Document 4: Organic EL Symposium, the 3rd Regular presentation Preprints, pp. 13 to 14 (2006)

SUMMARY OF THE INVENTION

Technical Problem

An object of the present invention is to provide a material for an organic EL device that is excellent in hole injection and transport abilities, electron blocking ability, thin film stability, and durability, as a material for an organic EL device with high efficiency and high durability, and also to provide an organic EL device having a high efficiency, a low driving voltage, and a long lifetime by combining the material with various materials for an organic EL device that is excellent in hole and electron injection and transport abilities, electron blocking ability, thin film stability, and durability, in such a manner that the characteristics of the materials can be effectively exhibited.

Physical properties of the organic compound to be provided by the present invention include (1) good hole injection characteristics, (2) large hole mobility, (3) electron blocking ability, (4) stability in a thin-film state, and (5) excellent heat resistance. Physical properties of the organic EL device to be provided by the present invention include (1) high luminous efficiency and high-power efficiency, (2) low turn on voltage, (3) low actual driving voltage, and (4) a long lifetime.

Solution to Problem

For achieving the object, the present inventors have focused the fact that an arylamine material having a specific structure is excellent in hole injection/transport ability, thin film stability, and durability. The arylamine compound of the above was selected to prepare an organic EL device, and the characteristics of the device were evaluated diligently. As a result, the present inventors have found that when an arylamine compound having a specific structure is selected as a material for the hole transport layer, holes injected from the anode side can be efficiently transported. Furthermore, various organic EL devices combining light-emitting materials having a specific structure and the like were manufactured, and the characteristics of the devices were evaluated diligently. As a result, they have completed the present invention.

Specifically, according to the present invention, the following organic EL devices are provided.

1) An organic EL device comprising at least an anode, a hole transport layer, a light emitting layer, an electron transport layer, and a cathode in this order, wherein the hole transport layer comprises an arylamine compound of the following general formula (1):

[Chemical Formula 1]

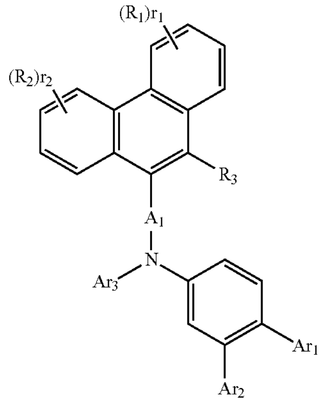

(1)

In the formula, $R_1$ and $R_2$ represent a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group. $R_3$ represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group. $A_1$ represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics. $Ar_1$ to $Ar_3$ represent a substituted or unsubstituted aromatic hydrocarbon group, a substituted or unsubstituted aromatic heterocyclic group, or a substituted or unsubstituted condensed polycyclic aromatic group. $r_1$ and $r_2$ represent integers from 0 to 4.

2) The organic EL device of 1), wherein the hole transport layer has a two-layer structure of a first hole transport layer and a second hole transport layer, and the second hole transport layer includes the arylamine compound of the general formula (1).

3) The organic EL device of 1) or 2), wherein the arylamine compound represented by the general formula (1) is an arylamine compound represented by the following general formula (1a).

[Chemical Formula 2]

(1a)

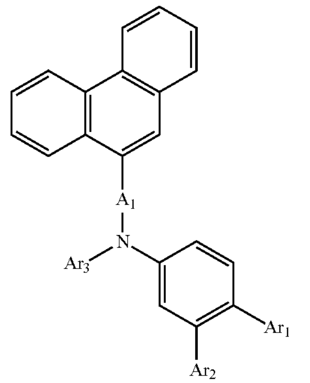

In the formula, $A_1$ and $Ar_1$ to $Ar_3$ represent as defined by the general formula (1).

4) The organic EL device of any one of 1) to 3), wherein $Ar_3$ in the general formula (1) or the general formula (1a) represents a substituted or unsubstituted phenyl group.

5) The organic EL device of any one of 1) to 4), wherein $A_1$ in the general formula (1) or the general formula (1a) represents a divalent group that results from the removal of two hydrogen atoms from substituted or unsubstituted benzene (phenylene group).

6) The organic EL device of any one of 1) to 5), wherein the light emitting layer includes a blue light emitting dopant.

7) The organic EL device of 6), wherein the blue light emitting dopant is a pyrene derivative having a pyrene skeleton in the molecule.

8) The organic EL device of 6), wherein the blue light emitting dopant is a compound represented by the following general formula (2) or general formula (3).

[Chemical Formula 3]

(2)

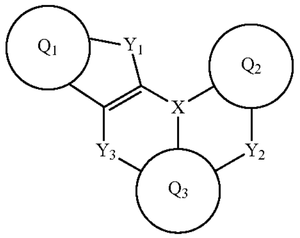

[Chemical Formula 4]

(3)

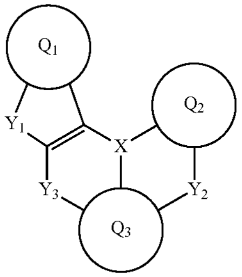

In the general formula (2) and the general formula (3), $Q_1$ to $Q_3$ may be the same or different, and represent a substituted or unsubstituted aromatic hydrocarbon, a substituted or unsubstituted condensed polycyclic aromatics, or a substituted or unsubstituted aromatic heterocyclic ring. X represents B, P, P=O, or P=S. $Y_1$ to $Y_3$ may be the same or different, and represent one of selected from N—$R_4$, $CR_5R_6$, O, S, Se and $SiR_7R_8$. $R_4$ to $R_8$ may be the same or different, and represent hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted condensed polycyclic aromatic group, or a substituted or unsubstituted aryloxy group. $R_5$ and $R_6$, and $R_7$ and $R_8$ may bind to each other to form a ring via a single bond, substituted or unsubstituted methylene, an oxygen atom, or a sulfur atom. When $Y_1$ to $Y_3$ are N—$R_4$, $CR_5R_6$, or $SiR_7R_8$, $R_4$ to $R_8$ may bind to $Q_1$, $Q_2$, or $Q_3$, which adjacent to $R_4$ to $R_8$ respectively, to form a ring via a linking group, such as substituted or unsubstituted methylene, an oxygen atom, a sulfur atom, or a monosubstituted amino group.

9) The organic EL device of any one of 1) to 8), wherein the light emitting layer includes an anthracene derivative having an anthracene skeleton in the molecule.

10) The organic EL device of 9), wherein the light emitting layer includes a host material that is an anthracene derivative having an anthracene skeleton in the molecule.

Specific examples of the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_1$ to $R_3$ in the general formula (1) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group.

Specific examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_1$ to $R_3$ in the general formula (1) include a deuterium atom; cyano; nitro; halogen atoms such as a fluorine atom, a chlorine atom, a bromine atom, and an iodine atom; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl; disubstituted amino groups substituted with an aromatic hydrocarbon group or a condensed polycyclic aromatic group, such as diphenylamino, and dinaphthylamino; disubstituted amino groups substituted with an aromatic heterocyclic group, such as dipyridylamino, and dithienylamino; and disubstituted amino groups substituted with a substituent selected from an aromatic hydrocarbon group, a condensed polycyclic aromatic group, or an aromatic heterocyclic group. These substituents may be further substituted with the exemplified substituents above.

Specific examples of the "linear or branched alkyloxy group of 1 to 6 carbon atoms" or the "cycloalkyloxy group of 5 to 10 carbon atoms" in the "linear or branched alkyloxy group of 1 to 6 carbon atoms that may have a substituent" or the "cycloalkyloxy group of 5 to 10 carbon atoms that may have a substituent" represented by $R_1$ to $R_3$ in the general formula (1) include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group. These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_1$ to $R_3$ in the general formula (1).

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_3$ in the general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

These groups may have a substituent, and specific examples of the substituent include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenyl, terphenyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl; disubstituted amino groups substituted with an aromatic hydrocarbon group or a condensed polycyclic aromatic group, such as diphenylamino, and dinaphthylamino; disubstituted amino groups substituted with an aromatic heterocyclic group, such as dipyridylamino, and dithienylamino; and disubstituted amino groups substituted with a substituent selected from an aromatic hydrocarbon group, a condensed polycyclic aromatic group, or an aromatic heterocyclic group. These substituents may be further substituted with the exemplified substituents above.

Specific examples of the "aryloxy group" in the "substituted or unsubstituted aryloxy group" represented by $R_1$ to $R_3$ in the general formula (1) include a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group.

These groups may have a substituent, and examples of the substituent include the same substituents exemplified as the "substituent" that the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_3$ in the general formula (1) may have.

Specific examples of the "aromatic hydrocarbon", the "aromatic heterocyclic ring", or the "condensed polycyclic aromatics" of the "substituted or unsubstituted aromatic hydrocarbon", the "substituted or unsubstituted aromatic heterocyclic ring", or the "substituted or unsubstituted condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_1$ in the general formula (1) include benzene, biphenyl, terphenyl, tetrakisphenyl, styrene, naphthalene, anthracene, acenaphthalene, fluorene, phenanthrene, indane, pyrene, triphenylene, pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

The "divalent group of aromatic hydrocarbon", the "divalent group of aromatic heterocyclic ring", or the "divalent group of condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_1$ in the general formula (1) is a divalent group that results from the removal of two hydrogen atoms from the above "aromatic hydrocarbon", "aromatic heterocyclic ring", or "condensed polycyclic aromatics". These groups may have a substituent, and examples of the substituent include the same substituents exemplified as the "substituent" that the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_3$ in the general formula (1) may have.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_3$ in the general formula (1) include phenyl, biphenyl, terphenyl, naphthyl, anthracenyl, phenanthryl, fluorenyl, indenyl, pyrenyl, perylenyl, fluoranthenyl, triphenylenyl, pyridyl, pyridinyl, triazinyl, furyl, pyrrolyl, thienyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

These groups may have a substituent, and examples of the substituent include the same substituents exemplified as the "substituent" that the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_3$ in the general formula (1) may have.

In the general formula (1) or the general formula (1a), $A_1$ is preferably the "divalent group of a substituted or unsubstituted aromatic hydrocarbon" or the "substituted or unsubstituted condensed polycyclic aromatic group", far preferably, a divalent group that results from the removal of two hydrogen atoms from benzene, biphenyl, or naphthalene, particularly preferably a divalent group that results from the removal of two hydrogen atoms from benzene.

In the general formula (1) or the general formula (1a), $Ar_1$ is preferably a "substituted or unsubstituted aromatic hydrocarbon group", a "substituted or unsubstituted condensed polycyclic aromatic group", a carbazolyl group, an indolyl group, a dibenzofuranyl group or a dibenzothienyl group, far preferably, a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted anthracenyl group, a substituted or unsubstituted fluorenyl group, a substituted or unsubstituted carbazolyl group, a substituted or unsubstituted indolyl group, a substituted or unsubstituted dibenzofuranyl group, or a substituted or unsubstituted dibenzothienyl group, particularly preferably a substituted or unsubstituted phenyl group.

In the general formula (1) or the general formula (1a), $Ar_2$ is preferably a "substituted or unsubstituted aromatic hydrocarbon group", or a "substituted or unsubstituted condensed polycyclic aromatic group", far preferably, a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted anthracenyl group, a substituted or unsubstituted fluorenyl group, particularly preferably a substituted or unsubstituted phenyl group.

In the general formula (1) or the general formula (1a), Ara is preferably a "substituted or unsubstituted aromatic hydrocarbon group", or a "substituted or unsubstituted condensed polycyclic aromatic group", far preferably, a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, particularly preferably a substituted or unsubstituted phenyl group.

Further, among the compounds of the general formula (1), the compounds of the general formula (1a) are far preferable.

Specific examples of the "aromatic hydrocarbon", the "condensed polycyclic aromatics", or the "aromatic heterocyclic ring" in the "substituted or unsubstituted aromatic hydrocarbon", the "substituted or unsubstituted condensed polycyclic aromatics", or the "substituted or unsubstituted aromatic heterocyclic ring" represented by $Q_1$ to $Q_3$ in the general formula (2) and the general formula (3) include benzene, naphthalene, anthracene, fluorene, phenanthrene, pyridine, pyrimidine, triazine, pyrrole, furan, thiophene, quinoline, isoquinoline, indene, benzofuran, benzothiophene, indole, indoline, carbazole, carboline, benzoxazole, benzothiazole, quinoxaline, benzimidazole, pyrazole, dibenzofuran, dibenzothiophene, naphthyridine, phenanthroline, and acridine.

These may have a substituent, and examples of the substituent include the same substituents exemplified as the "substituent" that the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_3$ in the general formula (1) may have. These substituents may bind to each other via a single bond, substituted or unsubstituted methylene, an oxygen atom, or a sulfur atom to form a ring.

X in the general formula (2) and the general formula (3) represents B, P, P═O, or P═S. B is defined as a boron atom, P is a phosphorus atom, P═O is a phosphorus atom in which an oxygen atom is bonded by a double bond, and P═S is defined as a phosphorus atom in which a sulfur atom is bonded by a double bond.

$Y_1$ to $Y_3$ in the general formula (2) and the general formula (3) may be the same or different, and represent one of selected from N—$R_4$, $CR_5R_6$, O, S, Se, and $SiR_7R_8$. N—$R_4$ is a nitrogen atom having $R_4$ as a substituent, $CR_5R_6$ is a carbon atom having $R_5$ and $R_6$ as a substituent, O is an oxygen atom, S is a sulfur atom, Se is a selenium atom, and $SiR_7R_8$ is a silicon atom having $R_7$ and $R_8$ as a substituent. The definitions of $R_4$ to $R_8$ will be further described in detail below.

When $Y_1$ to $Y_3$ in the general formula (2) and the general formula (3) are N—$R_4$, $CR_5R_6$, or $SiR_7R_8$, specific examples of the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_4$ to $R_8$ in N—$R_4$, $CR_5R_6$, or $SiR_7R_8$ include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_1$ to $R_3$ in the general formula (1).

When $Y_1$ to $Y_3$ in the general formula (2) and the general formula (3) are N—$R_4$, $CR_5R_6$, or $SiR_7R_8$, specific examples of the "linear or branched alkyloxy group of 1 to 6 carbon atoms" or the "cycloalkyloxy group of 5 to 10 carbon atoms" in the "linear or branched alkyloxy group of 1 to 6 carbon atoms that may have a substituent" or the "cycloalkyloxy group of 5 to 10 carbon atoms that may have a substituent" represented by $R_4$ to $R_8$ in N—$R_4$, $CR_5R_6$, or $SiR_7R_8$ include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_1$ to $R_3$ in the general formula (1).

When $Y_1$ to $Y_3$ in the general formula (2) and the general formula (3) are N—$R_4$, $CR_5R_6$, or $SiR_7R_8$, specific examples of the "aromatic hydrocarbon group", or the "condensed polycyclic aromatic group" in the "substituted or unsubstituted aromatic hydrocarbon group", or the "substituted or unsubstituted condensed polycyclic aromatic group" represented by $R_4$ to $R_8$ in N—$R_4$, $CR_5R_6$, or $SiR_7R_8$ include phenyl, biphenyl, terphenyl, naphthyl, anthracenyl, phenanthryl.

These groups may have a substituent, and examples of the substituent include the same substituents exemplified as the "substituent" that the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_3$ in the general formula (1) may have.

When $Y_1$ to $Y_3$ in the general formula (2) and the general formula (3) are N—$R_4$, $CR_5R_6$, or $SiR_7R_8$, specific examples of the "aryloxy group" in the "substituted or unsubstituted aryloxy group" represented by $R_4$ to $R_8$ in N—$R_4$, $CR_5R_6$, or $SiR_7R_8$ include a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group.

These groups may have a substituent, and examples of the substituent include the same substituents exemplified as the "substituent" that the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_3$ in the general formula (1) may have.

In the general formulas (2) and the general formula (3), the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Q_1$ to $Q_3$ are preferably benzene, naphthalene, phenanthrene, pyridine, pyrimidine, indene, benzofuran, benzothiophene, and indol, far preferably, benzene and naphthalene.

In the general formula (2) and the general formula (3), when $Y_1$ to $Y_3$ are N—$R_4$, $CR_5R_6$, or $SiR_7R_8$, $R_4$ to $R_8$ in N—$R_4$, $CR_5R_6$, or $SiR_7R_8$ are preferably a "linear or branched alkyl group of 1 to 6 carbon atoms that may have a substituent", a "cycloalkyl group of 5 to 10 carbon atoms that may have a substituent", a "linear or branched alkenyl group of 2 to 6 carbon atoms that may have a substituent", a "linear or branched alkyloxy group of 1 to 6 carbon atoms that may have a substituent", a "cycloalkyloxy group of 5 to 10 carbon atoms that may have a substituent", a "substituted or unsubstituted aromatic hydrocarbon group", a "substituted or unsubstituted condensed polycyclic aromatic group", or a "substituted or unsubstituted aryloxy group", $R_4$ in N—$R_4$ is far preferably a "linear or branched alkyl group of 1 to 6 carbon atoms that may have a substituent", a "cycloalkyl group of 5 to 10 carbon atoms that may have a substituent", a "linear or branched alkenyl group of 2 to 6 carbon atoms that may have a substituent", a "substituted or unsubstituted aromatic hydrocarbon group", a "substituted or unsubstituted condensed polycyclic aromatic group".

In the general formula (2) and the general formula (3), $Y_1$ is preferably N—$R_4$, O, or S, far preferably, O, or S. In the general formula (2) and the general formula (3), it is preferable that at least one of $Y_1$ and $Y_2$ is N—$R_4$, far preferably, both of $Y_1$ and $Y_2$ is N—$R_4$. $R_4$ in N—$R_4$ is preferably a "substituted or unsubstituted aromatic hydrocarbon group", or a "substituted or unsubstituted condensed polycyclic aromatic group", far preferably, a substituted or unsubstituted phenyl group, a substituted or unsubstituted biphenyl group, a substituted or unsubstituted terphenyl group, or a substituted or unsubstituted naphthyl group.

Effects of the Invention

The arylamine compounds of the general formula (1), for preferred use in the organic EL device of the present invention, can be used as a constitutive material of a hole transport layer of an organic EL device. The arylamine compounds of the general formula (1) have (1) good hole injection characteristics, (2) large hole mobility, (3) excellent electron blocking ability, (4) stability in a thin-film state, and (5) excellent heat resistance.

The high efficiency, low turn on voltage, and high durability of the organic EL device in the present invention can be achieved because of the use of the arylamine compound, which has greater hole mobility, superior electron blocking ability, superior amorphousness, and a more stable thin-film state than conventional hole transport materials.

Further, in the present invention, the hole transport layer has a two-layer structure of a first hole transport layer and a second hole transport layer, and the second hole transport layer located on the light emitting layer side includes the arylamine compound represented by the general formula (1), and thus, the electron blocking performance of the arylamine compound can be fully utilized. Thus, a more efficient, and high durability of the organic EL device can be realized.

MODE FOR CARRYING OUT THE INVENTION

The specific examples of preferred compounds among the arylamine compounds represented by the general formula (1) preferably used in the organic EL device of the present invention is showing in FIGS. 1 to 6. The present invention, however, is not restricted to these compounds.

Figure 1:
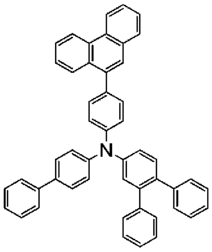
FIG. 1 is a figure showing the structural formula of the compound 1-1 to 1-15 as an arylamine compound represented by the general formula (1).
Figure 1:
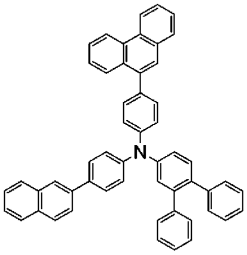
Figure 1:
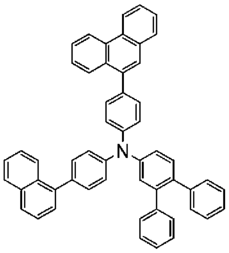
Figure 1:
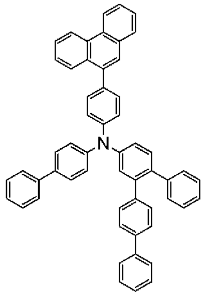
Figure 1:
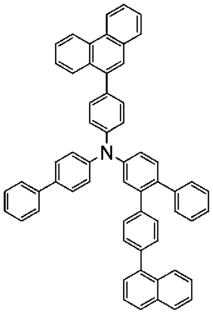
Figure 1:
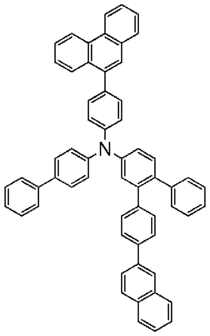
Figure 1:
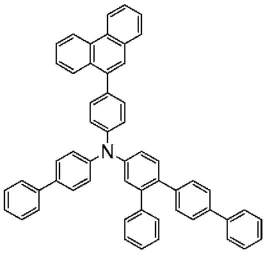
Figure 1:
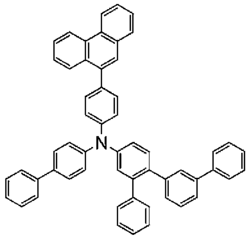
Figure 1:
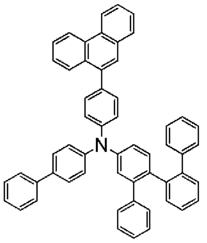
Figure 1:
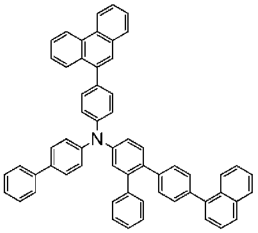
Figure 1:
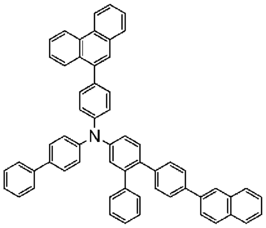
Figure 1:
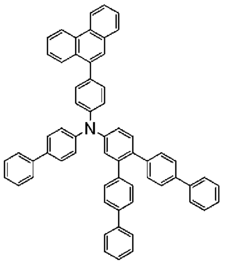
Figure 1:
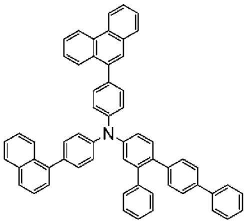
Figure 1:
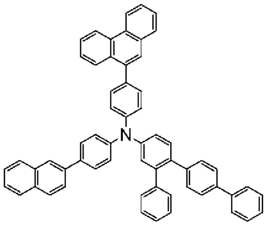
Figure 1:
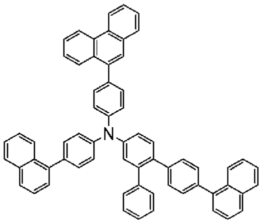
Figure 2:
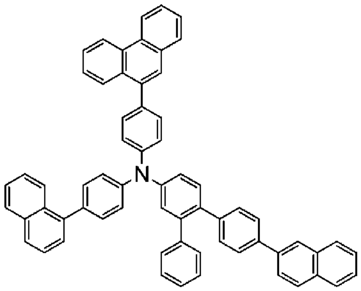
FIG. 2 is a figure showing the structural formula of the compound 1-16 to 1-20 as an arylamine compound represented by the general formula (1).
Figure 2:
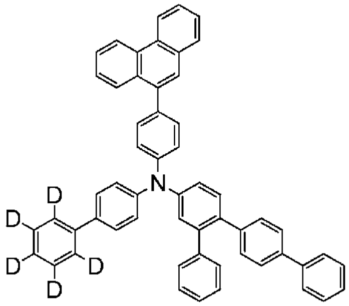
Figure 2:
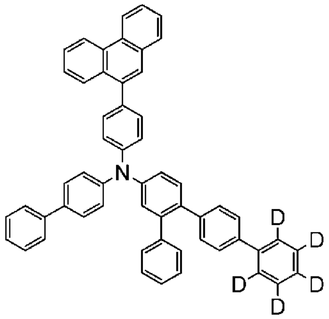
Figure 2:
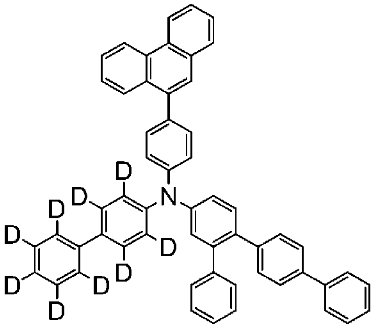
Figure 2:
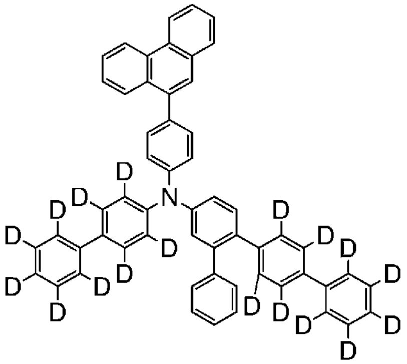
Figure 3:
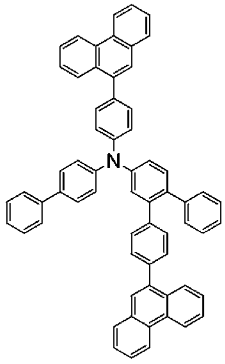
FIG. 3 is a figure showing the structural formula of the compound 1-21 to 1-31 as an arylamine compound represented by the general formula (1).
Figure 3:
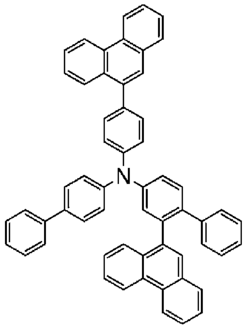
Figure 3:
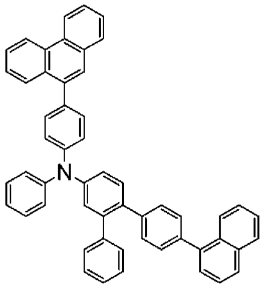
Figure 3:
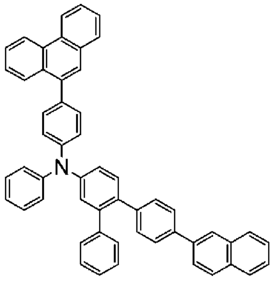
Figure 3:
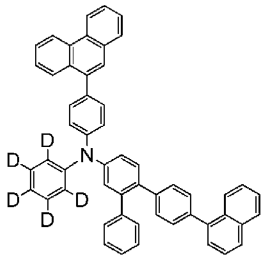
Figure 3:
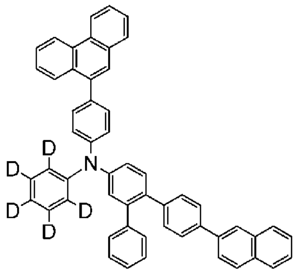
Figure 3:
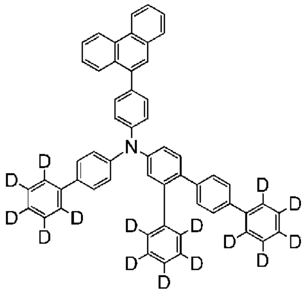
Figure 3:
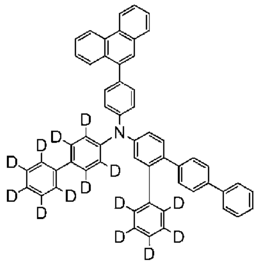
Figure 3:
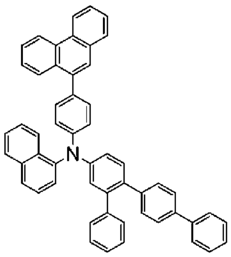
Figure 3:
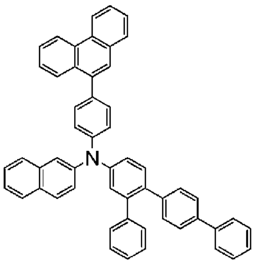
Figure 3:
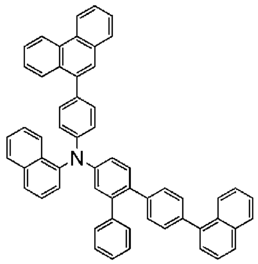
Figure 4:
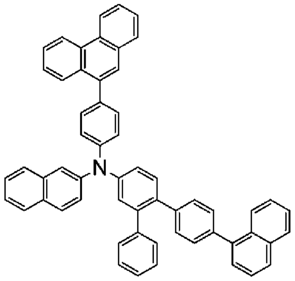
FIG. 4 is a figure showing the structural formula of the compound 1-32 to 1-42 as the arylamine compound represented by the general formula (1).
Figure 4:
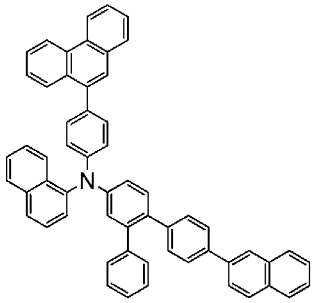
Figure 4:
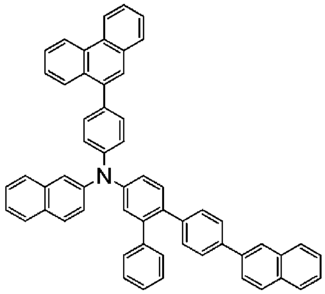
Figure 4:
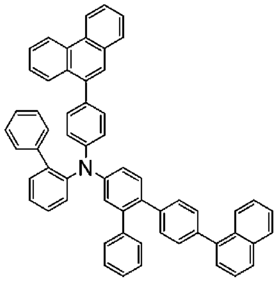
Figure 4:
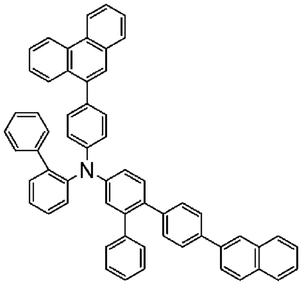
Figure 4:
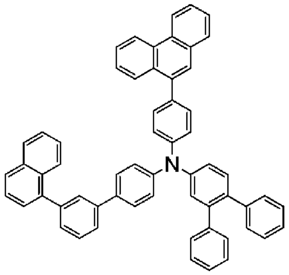
Figure 4:
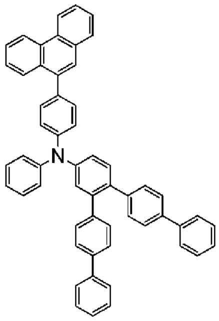
Figure 4:
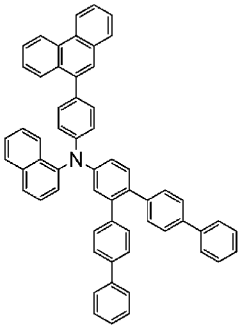
Figure 4:
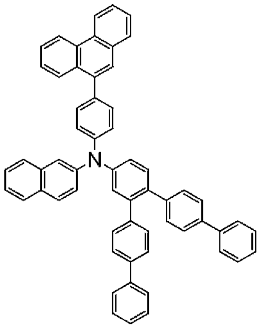
Figure 4:
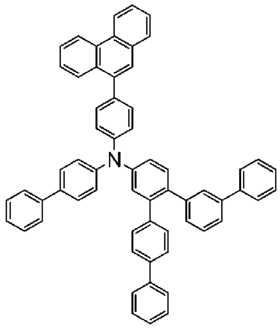
Figure 4:
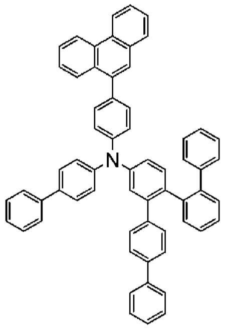
Figure 5:
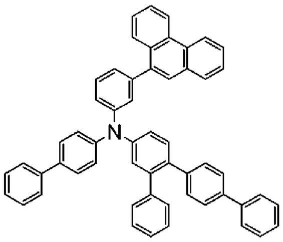
FIG. 5 is a figure showing the structural formula of the compound 1-43 to 1-55 as the arylamine compound represented by the general formula (1).
Figure 5:
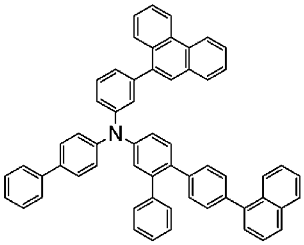
Figure 5:
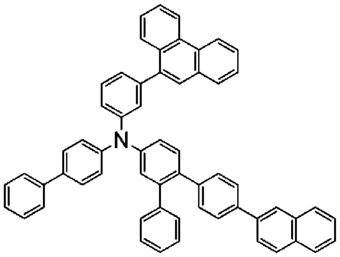
Figure 5:
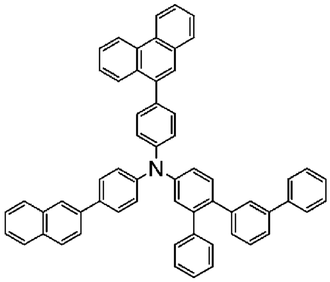
Figure 5:
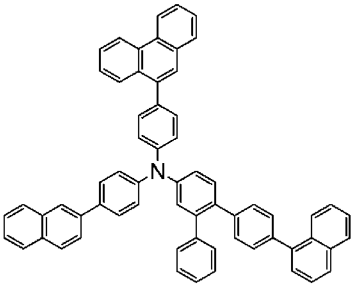
Figure 5:
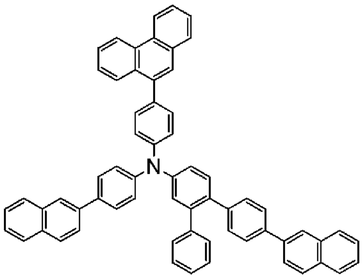
Figure 5:
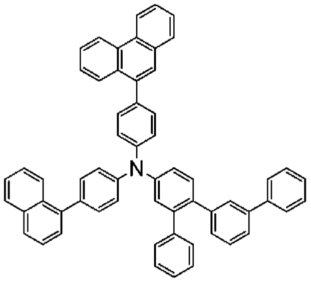
Figure 5:
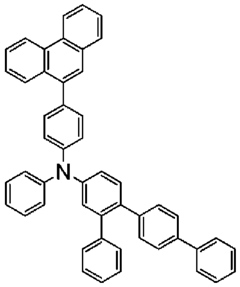
Figure 5:
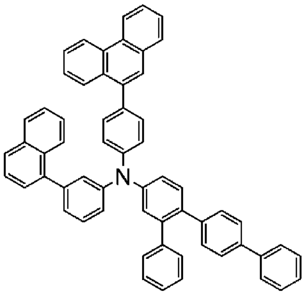
Figure 5:
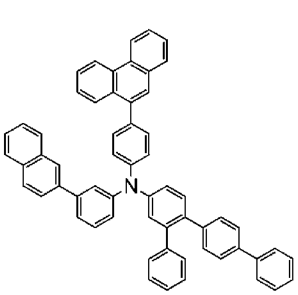
Figure 5:
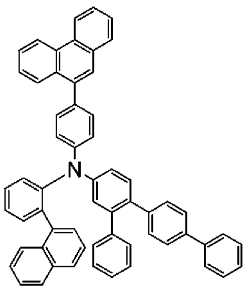
Figure 5:
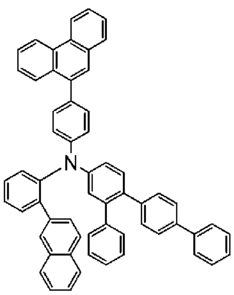
Figure 5:
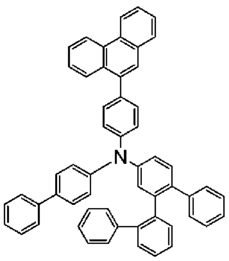
Figure 6:
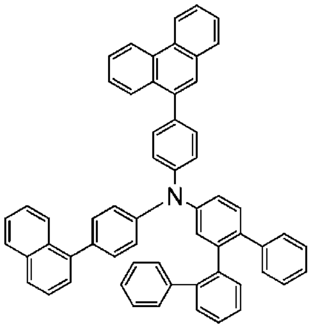
FIG. 6 is a figure showing the structural formula of the compound 1-56 to 1-64 as an arylamine compound represented by the general formula (1).
Figure 6:
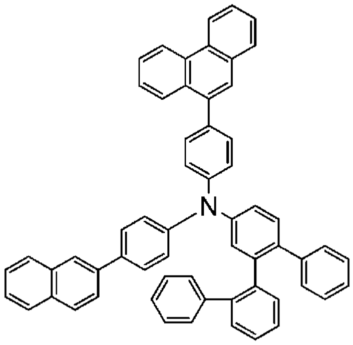
Figure 6:
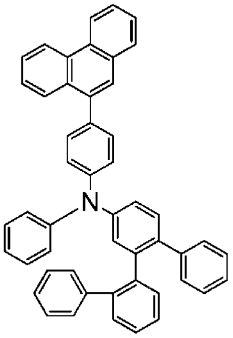
Figure 6:
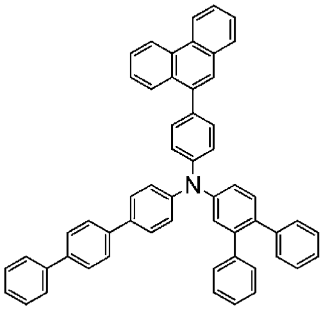
Figure 6:
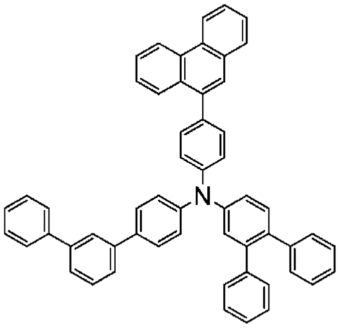
Figure 6:
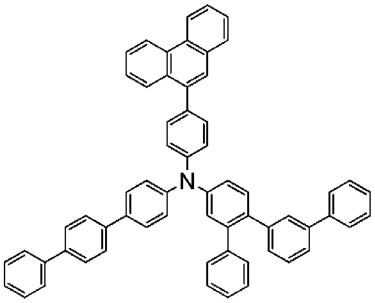
Figure 6:
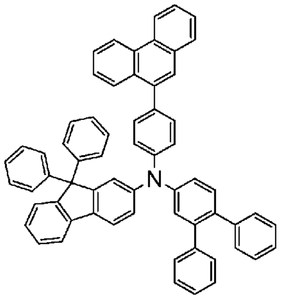
Figure 6:
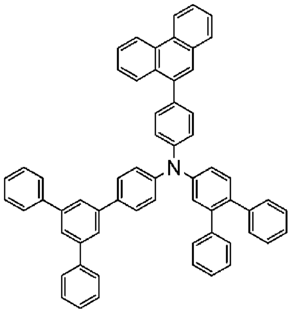
Figure 6:
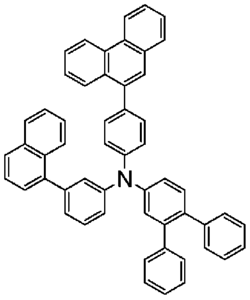
Figure 7:
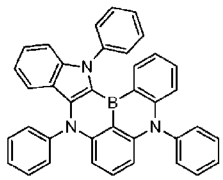
FIG. 7 is a figure showing the structural formula of the compound 2-1 to 2-15 as a compound represented by the general formula (2).
Figure 7:
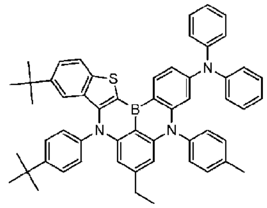
Figure 7:
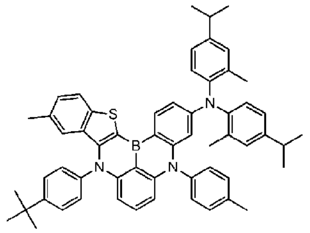
Figure 7:
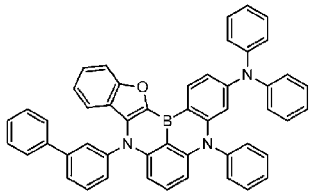
Figure 7:
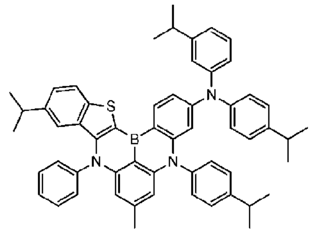
Figure 7:
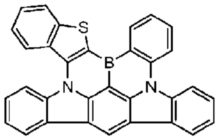
Figure 7:
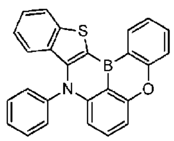
Figure 7:
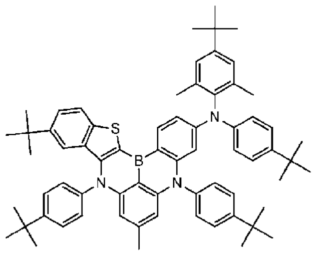
Figure 7:
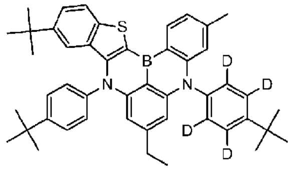
Figure 7:
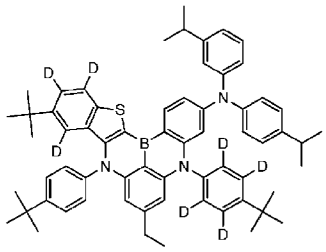
Figure 7:
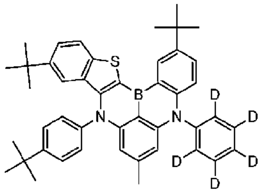
Figure 7:
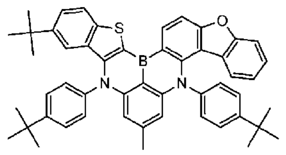
Figure 7:
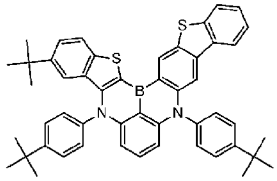
Figure 7:
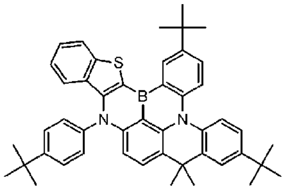
Figure 7:
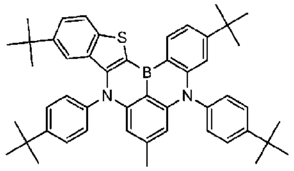
Figure 8:
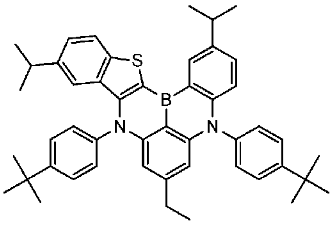
FIG. 8 is a figure showing the structural formula of the compound 2-16 to 2-22 as the compound represented by the general formula (2).
Figure 8:
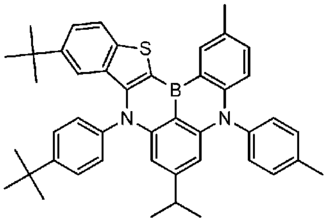
Figure 8:
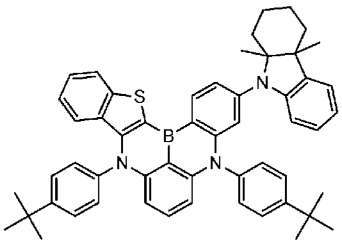
Figure 8:
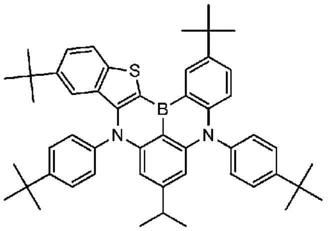
Figure 8:
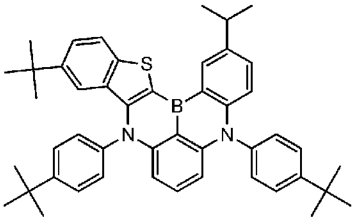
Figure 8:
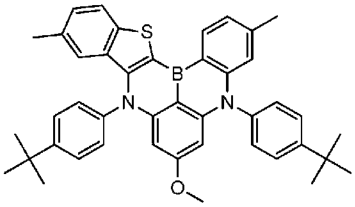
Figure 8:
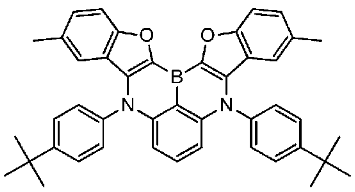
Figure 9:
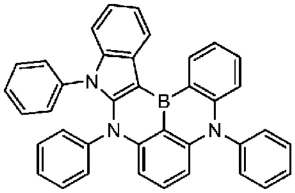
FIG. 9 is a figure showing the structural formula of the compound 3-1 to 3-8 as a compound represented by the general formula (3).
Figure 9:
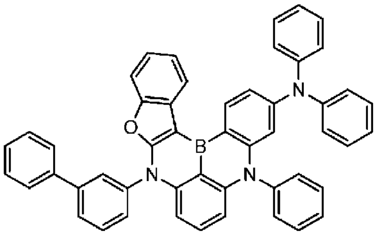
Figure 9:
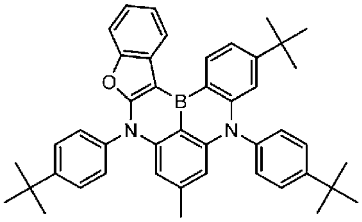
Figure 9:
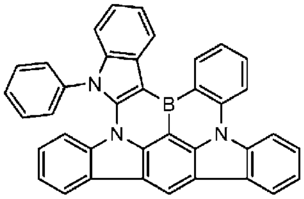
Figure 9:
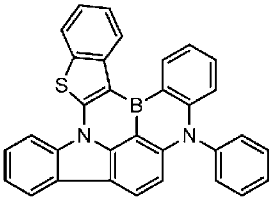
Figure 9:
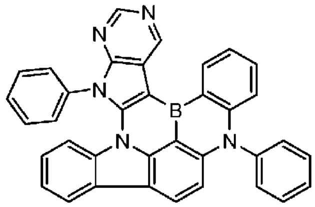
Figure 9:
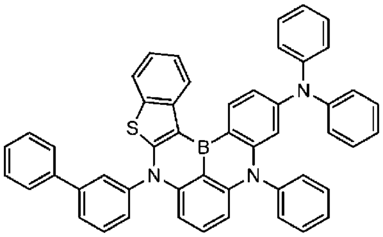
Figure 9:
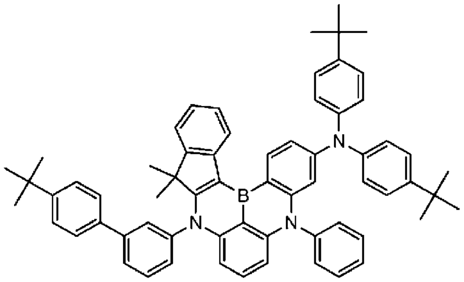

The specific examples of preferred compounds among the compounds represented by the general formula (2) or the general formula (3) preferably used in the organic EL device of the present invention is showing in FIG. 7 to 8 or 9. The present invention, however, is not restricted to these compounds.

The arylamine compounds of the general formula (1) were purified by methods such as column chromatography, adsorption using, for example, a silica gel, activated carbon, or activated clay, recrystallization or crystallization using a solvent, and a sublimation purification method. The compounds were identified by an NMR analysis. A glass transition point (Tg), and a work function were measured as material property values. The glass transition point (Tg) can be used as an index of stability in a thin-film state, and the work function can be used as an index of hole transportability and electron blocking performance.

Other compounds used for the organic EL device of the present invention were purified by methods such as column chromatography, adsorption using, for example, a silica gel, activated carbon, or activated clay, recrystallization or crystallization using a solvent, and a sublimation purification method, and finally purified by a sublimation purification method.

The glass transition point (Tg) was measured by a high-sensitive differential scanning calorimeter (DSC3100SA produced by Bruker AXS) using powder.

For the measurement of the work function, a 100 nm thin film was fabricated on an ITO substrate, and an ionization potential measuring device (PYS-202 produced by Sumitomo Heavy Industries, Ltd.) was used.

The organic EL device of the present invention may have a structure including an anode, a hole transport layer, a light emitting layer, an electron transport layer, and a cathode successively formed on a substrate, optionally with a hole injection layer between the anode and hole transport layer, a hole blocking layer between the light emitting layer and the electron transport layer, and an electron injection layer between the electron transport layer and the cathode. Some of the organic layers in the multilayer structure may be omitted, or may serve more than one function. For example, a single organic layer may serve as the hole injection layer and the hole transport layer, or as the electron injection layer and the electron transport layer, and so on. Further, any of the layers may be configured to laminate two or more organic layers having the same function, and the hole transport layer may have a two-layer laminated structure, the light emitting layer may have a two-layer laminated structure, the electron transport layer may have a two-layer laminated structure, and so on.

The organic EL device of the present invention is preferably configured such that the hole transport layer has a two-layer laminated structure of a first hole transport layer and a second hole transport layer. In this case, the second hole transport layer is preferably adjacent to a light emitting layer, and it can function as an electron blocking layer.

Electrode materials with high work functions such as ITO and gold are used as the anode of the organic EL device of the present invention. The hole injection layer of the organic EL device of the present invention may be made of, for example, various triphenylamine derivatives such as starburst-type triphenylamine derivatives and various triphenylamine tetramers; porphyrin compounds as represented by copper phthalocyanine; accepting heterocyclic compounds such as hexacyano azatriphenylene; and coating-type polymer materials. These materials may be formed into a thin film by a vapor deposition method or other known methods such as a spin coating method and an inkjet method.

The arylamine compounds of the general formula (1) are used as the hole transport layer of the organic EL device of the present invention. Examples of a hole transporting material that can be mixed or can be used at the same time with the arylamine compounds of the general formula (1) can be the organic amine compounds such as various triphenylamine derivatives such as arylamine compounds having a structure in which four triphenylamine structures are joined within a molecule via a single bond or a divalent group that does not contain a heteroatom; and arylamine compounds having a structure in which two triphenylamine structures are joined within a molecule via a single bond or a divalent group that does not contain a heteroatom, in addition to benzidine derivatives such as N,N'-diphenyl-N,N'-di(m-tolyl)benzidine (TPD), N,N'-diphenyl-N,N'-di(α-naphthyl)benzidine (NPD), and N,N,N',N'-tetrabiphenylylbenzidine; and 1,1-bis[4-(di-4-tolylamino)phenyl]cyclohexane (TAPC). These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin film by a vapor deposition method or other known methods such as a spin coating method and an inkjet method.

The material used for the hole injection layer or the hole transport layer may be obtained by p-doping materials such as trisbromophenylamine hexachloroantimony, and radialene derivatives (refer to Patent Document 6, for example) into a material commonly used for these layers, or may be, for example, polymer compounds each having, as a part of the compound structure, a structure of a benzidine derivative such as TPD.

In the case where the hole transport layer of the organic EL device of the present invention has a two-layer structure of a first hole transport layer and a second hole transport layer, the arylamine compounds of the general formula (1) are used as the second hole transport layer located on the light emitting layer side. Examples of a hole transporting material that can be mixed or can be used at the same time with the arylamine compounds of the general formula (1) can be compounds having an electron blocking effect, including, for example, carbazole derivatives such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis[4-(carbazol-9-yl)phenyl]adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene.

These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin film by using a vapor deposition method or other known methods such as a spin coating method and an inkjet method.

Material used for the light emitting layer of the organic EL device of the present invention can be preferably the compounds represented by the general formula (2) or the general formula (3). Furthermore, various metal complexes in addition to the quinolinol derivative metal complexes such as $Alq_3$; anthracene derivatives; bis(styryl)benzene derivatives; pyrene derivatives; oxazole derivatives; and polyparaphenylene vinylene derivatives can be used. Further, the light emitting layer may be made of a host material and a dopant material. In that case, as the host material, an anthracene derivative having an anthracene skeleton in the molecule is preferably used. Further, as the dopant material, a pyrene derivative having a pyrene skeleton in the molecule, and a compound represented by the general formula (2), or the general formula (3) are preferably used. Furthermore, heterocyclic compound having an indole ring as a partial structure of the fused ring; heterocyclic compound having a carbazole ring as a partial structure of fused ring; carbazole derivative; thiazole derivative; benzimidazole derivative; polydialkylfluorene derivative; quinacridone, coumarin, rubrene, perylene, derivatives thereof; benzopyran derivative; indenophenanthrene derivatives; rhodamine derivatives; and aminostyryl derivatives can be used. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent material. Phosphorescent materials as metal complexes of metals such as iridium and platinum may be used. Examples of the phosphorescent materials include green phosphorescent materials such as $Ir(ppy)_3$, blue phosphorescent materials such as Flrpic and FIr6, and red phosphorescent materials such as $Btp_2Ir(acac)$. Here, an anthracene derivative having an anthracene skeleton in the molecule is preferably used for the host material. Furthermore, carbazole derivatives such as 4,4'-di(N-carbazolyl)biphenyl (CBP), TCTA, and mCP may be used as the hole injecting and transporting host material.

Compounds such as p-bis(triphenylsilyl)benzene (UGH2) and 2,2',2"-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, Examples of the light-emitting material may be delayed fluorescent-emitting material such as a CDCB derivative of PIC-TRZ, CC2TA, PXZ-TRZ, 4CzIPN or the like (refer to Non-Patent Document 3, for example).

These materials may be formed into a thin film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproin (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin film by using a vapor deposition method or other known methods such as a spin coating method and an inkjet method.

The electron transport layer of the organic EL device of the present invention may be formed by using metal complexes of quinolinol derivatives such as $Alq_3$ and BAlq, various metal complexes, triazole derivatives, triazine derivatives, oxadiazole derivatives, pyridine derivatives, pyrimidine derivatives, benzimidazole derivatives, thiadiazole derivatives, anthracene derivatives, carbodiimide derivatives, quinoxaline derivatives, pyridoindole derivatives, phenanthroline derivatives, and silole derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; metal complexes of quinolinol derivatives such as lithium quinolinol; metal oxides such as aluminum oxide; and metals such as itterbium (Yb), samarium (Sm), calcium (Ca), strontium (Sr), cesium (Cs). However, the electron injection layer may be omitted in the preferred selection of the electron transport layer and the cathode.

Further, in the electron injection layer or the electron transport layer, a material obtained by further N-doping a material which is commonly used for the layer with a metal such as cecium, or the like can be used.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of (4-naphthalen-2-yl-phenyl)-(4-phenanthrene-9-yl-phenyl)-[1,1';2',1"]terphenyl-4'-yl-amine (1-2)

(4-naphthalene-2-yl-phenyl)-[1,1';2',1"]terphenyl-4'-yl-amine: 15.0 g, 9-(4-bromo-phenyl)-phenanthrene: 12.3 g, tert-butoxy sodium: 4.8 g, toluene: 240 mL were added into a reaction vessel, and the mixture was aerated with nitrogen gas under ultrasonic irradiation for 30 minutes. Then, palladium(II) acetate: 0.1 g, tri(tert-butyl)phosphine: 0.3 g were added thereto, and the mixture was refluxed and stirred for 4 hours. After allowing to cool, the filtrate obtained by filtration was concentrated under reduced pressure to obtain a crude product. The crude product was purified by recrystallizing with a toluene solvent, whereby a white powder of (4-naphthalen-2-yl-phenyl)-(4-phenanthrene-9-yl-phenyl)-[1,1';2',1"]terphenyl-4'-yl-amine (1-2): 18.7 g (yield: 80%) was obtained.

[Chemical Formula 5]

(1-2)

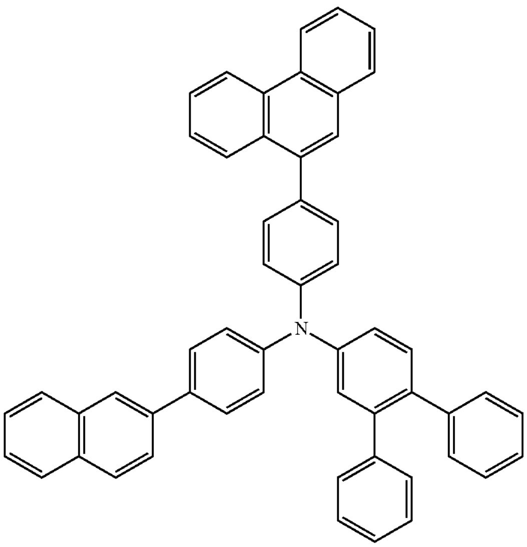

The structure of the obtained white powder was identified by NMR.

$^1$H-NMR ($CDCl_3$) detected 37 hydrogen signals, as follows. δ (ppm)=8.81 (1H), 8.76 (1H), 8.11 (1H), 8.09 (1H), 7.92 (4H), 7.80 (1H), 7.77 (2H), 7.75-7.58 (5H), 7.57-7.48 (4H), 7.48-7.30 (7H), 7.27-7.14 (10H).

Example 2

Synthesis of (4-naphthalen-1-yl-phenyl)-(4-phenanthrene-9-yl-phenyl)-[1,1';2',1"]terphenyl-4'-yl-amine (1-3)

(4-phenanthrene-9-yl-phenyl)-[1,1';2',1"]terphenyl-4'-yl-amine: 15.0 g, 1-(4-bromo-phenyl)-naphthalene: 9.4 g, tert-butoxy sodium: 4.3 g, toluene: 210 mL were added into a reaction vessel, and the mixture was aerated with nitrogen gas under ultrasonic irradiation for 30 minutes. Then, palladium(II) acetate: 0.1 g, tri(tert-butyl)phosphine: 0.1 g were added thereto, and the mixture was stirred under reflux overnight. After allowing to cool, the filtrate obtained by filtration was concentrated under reduced pressure to obtain a crude product. The crude product was purified using column chromatography (support: silica gel, eluent: dichloromethane/n-heptane), whereby a white powder of (4-naphthalen-1-yl-phenyl)-(4-phenanthrene-9-yl-phenyl)-[1,1';2',1"]terphenyl-4'-yl-amine (1-3): 15.9 g (yield: 76%) was obtained.

[Chemical Formula 6]

(1-3)

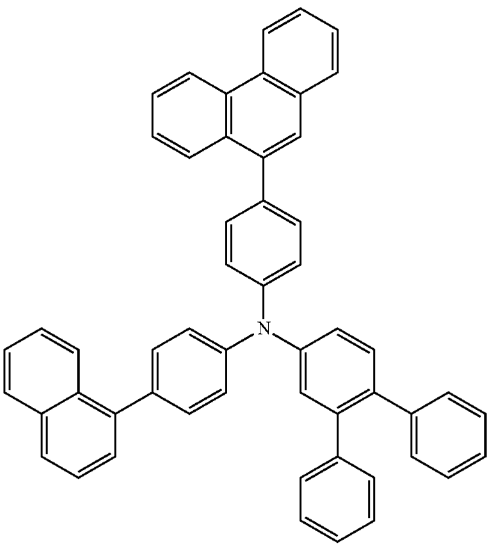

The structure of the obtained white powder was identified by NMR.

$^1$H-NMR ($CDCl_3$) detected 37 hydrogen signals, as follows. δ (ppm)=8.83 (1H), 8.77 (1H), 8.12 (2H), 7.95 (2H), 7.89 (1H), 7.80 (1H), 7.77-7.60 (5H), 7.60-741 (14H), 7.38 (1H), 7.28-7.17 (9H).

Example 3

Synthesis of biphenyl-4-yl-(4-phenanthrene-9-yl-phenyl)-[1,1';2',1";4",1'"]quarterphenyl-4'-yl-amine (1-4)

Biphenyl-4-yl-(6-bromo-[1,1';4',1"]terphenyl-3-yl)-(4-phenanthrene-9-yl-phenyl)-amine: 10.0 g, phenylboronic acid: 2.5 g, potassium carbonate: 3.6 g, toluene: 80 mL, ethanol: 30 mL, and water: 30 mL were added into a reaction vessel, and the mixture was aerated with nitrogen gas under ultrasonic irradiation for 30 minutes. Then, tetrakis(triphenylphosphine)palladium (0): 0.3 g was added thereto, and the mixture was stirred under reflux overnight. After allowing to cool, an organic layer was separated and extracted by liquid separation, and the organic layer was concentrated under reduced pressure to obtain a crude product. The crude product was purified by crystallization with a mixed solvent of dichloromethane/acetone, whereby a white powder of biphenyl-4-yl-(4-phenanthrene-9-yl-phenyl)-[1,1';2',1";4",1'"]quarterphenyl-4'-yl-amine (1-4): 5.4 g (yield: 54%) was obtained.

[Chemical Formula 7]

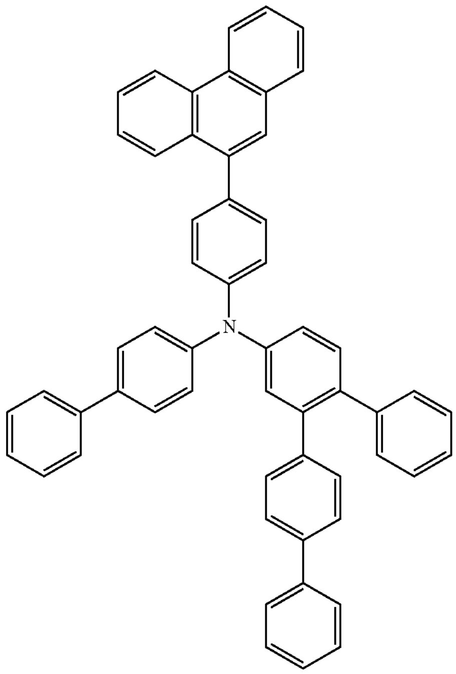

(1-4)

The structure of the obtained white powder was identified by NMR.

$^1$H-NMR ($CDCl_3$) detected 39 hydrogen signals, as follows. δ (ppm)=8.82 (1H), 8.76 (1H), 8.11 (1H), 7.94 (1H), 7.78 (1H), 7.75-7.56 (10H), 7.56-7.37 (15H), 7.37-7.30 (3H), 7.27-7.20 (6H).

Example 4

Synthesis of biphenyl-4-yl-(4-phenanthrene-9-yl-phenyl)-(4"-naphthalene-1-yl-[1,1';2',1"]terphenyl-4'-yl)-amine (1-5)

Biphenyl-4-yl-(6-bromo-4'-naphthalene-1-yl-biphenyl-3-yl)-(4-phenanthrene-9-yl-phenyl)-amine: 10.0 g, phenylboronic acid: 2.3 g, potassium carbonate: 3.4 g, toluene: 80 mL, ethanol: 30 mL, and water: 30 mL were added into a reaction vessel, and the mixture was aerated with nitrogen gas under ultrasonic irradiation for 30 minutes. Then, tetrakis(triphenylphosphine)palladium (0): 0.3 g was added thereto, and the mixture was stirred under reflux overnight. After allowing to cool, an organic layer was separated and extracted by liquid separation, and the organic layer was concentrated under reduced pressure to obtain a crude product. The crude product was purified using column chromatography (support: silica gel, eluent: dichloromethane/n-heptane), whereby a white powder of biphenyl-4-yl-(4-phenanthrene-9-yl-phenyl)-(4"-naphthalene-1-yl-[1,1';2',1"]terphenyl-4'-yl)-amine (1-5)): 2.8 g (yield: 28%) was obtained.

[Chemical Formula 8]

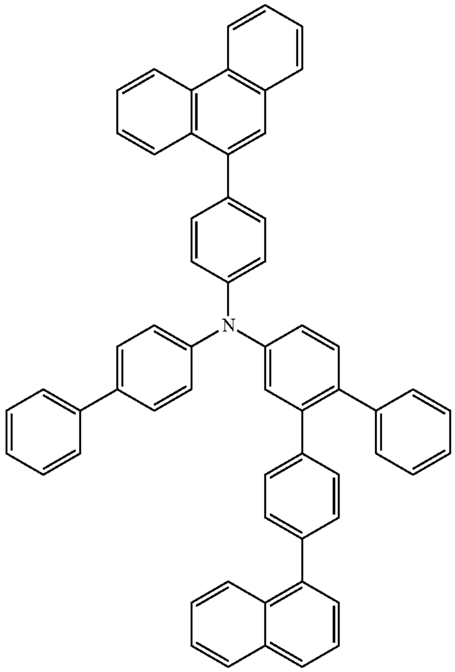

(1-5)

The structure of the obtained white powder was identified by NMR.

$^1$H-NMR ($CDCl_3$) detected 41 hydrogen signals, as follows. δ (ppm)=8.82 (1H), 8.76 (1H), 8.13 (1H), 7.91 (4H), 7.79 (1H), 7.76-7.58 (8H), 7.58-7.39 (14H), 7.39-7.25 (11H).

Example 5

Synthesis of biphenyl-4-yl-(4-phenanthrene-9-yl-phenyl)-(4"-naphthalen-2-yl-[1,1';2',1"]terphenyl-4'-yl)-amine (1-6)

Biphenyl-4-yl-(6-bromo-4'-naphthalene-2-yl-biphenyl-3-yl)-(4-phenanthrene-9-yl-phenyl)-amine: 10.0 g, phenylboronic acid: 2.3 g, potassium carbonate: 3.4 g, toluene: 80 mL, ethanol: 30 mL, and water: 30 mL were added into a reaction vessel, and the mixture was aerated with nitrogen gas under ultrasonic irradiation for 30 minutes. Then, tetrakis(triphenylphosphine)palladium (0): 0.3 g was added thereto, and the mixture was stirred under reflux overnight. After allowing to cool, an organic layer was separated and extracted by liquid separation, and the organic layer was concentrated under reduced pressure to obtain a crude product. The crude product was purified by crystallization with a mixed solvent of dichloromethane/acetone, whereby a white powder of biphenyl-4-yl-(4-phenanthrene-9-yl-phenyl)-(4"-naphthalen-2-yl-[1,1';2',1"]terphenyl-4'-yl)-amine (1-6): 5.8 g (yield: 58%) was obtained.

[Chemical Formula 9]

(1-6)

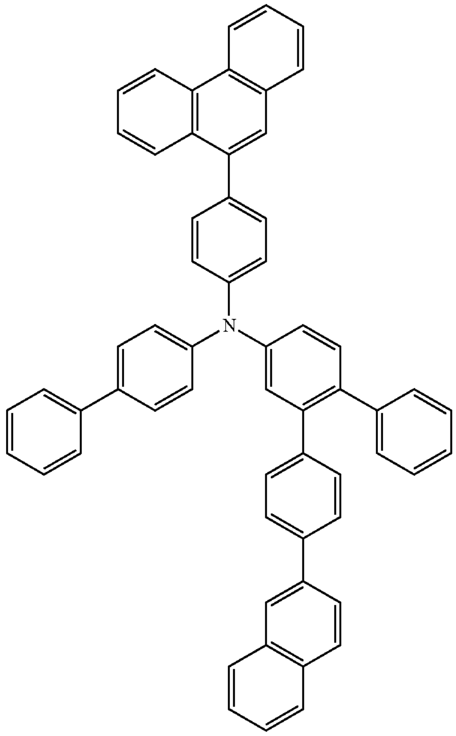

The structure of the obtained white powder was identified by NMR.

$^1$H-NMR ($CDCl_3$) detected 41 hydrogen signals, as follows. δ (ppm)=8.83 (1H), 8.77 (1H), 8.14 (1H), 8.05 (1H), 7.91 (4H), 7.79 (1H), 7.78-7.59 (11H), 7.59-7.34 (12H), 7.34-7.22 (9H).

Example 6

Synthesis of biphenyl-4-yl-(4-phenanthrene-9-yl-phenyl)-[1,2';1',1";4",1'"]quarterphenyl-4'-yl-amine (1-7)

Biphenyl-4-yl-[1,2';1',1";4",1'"]quarterphenyl-4'-yl-amine: 14.5 g, 9-(4-bromo-phenyl)-phenanthrene: 9.3 g, tert-butoxy sodium: 3.2 g, toluene: 93 mL were added into a reaction vessel, and the mixture was aerated with nitrogen gas under ultrasonic irradiation for 30 minutes. Then, palladium(II) acetate: 0.1 g, tri(tert-butyl)phosphine: 0.2 g were added thereto, and the mixture was refluxed and stirred for 3 hours. After allowing to cool, a crude product precipitated by adding water was collected by filtration. The crude product was purified by crystallization with a mixed solvent of monochlorobenzene/acetone, whereby a white powder of biphenyl-4-yl-(4-phenanthrene-9-yl-phenyl)-[1,2';1',1";4",1'"]quarterphenyl-4'-yl-amine (1-7): 14.0 g (yield: 69%) was obtained.

[Chemical Formula 10]

(1-7)

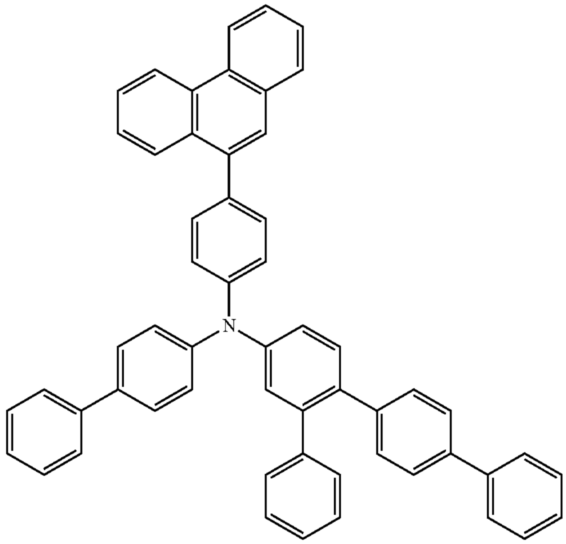

The structure of the obtained white powder was identified by NMR.

$^1$H-NMR ($CDCl_3$) detected 39 hydrogen signals, as follows. δ(ppm)=8.84 (1H), 8.77 (1H), 8.14 (1H), 7.90 (1H), 7.80 (1H), 7.78-7.60 (10H), 7.60-7.33 (17H), 7.33-7.20 (7H).

Example 7

Synthesis of biphenyl-4-yl-(4-phenanthrene-9-yl-phenyl)-[1,1';4',1";2",1'":4'",1""]quinquephenyl-4"-yl-amine (1-12)

The reaction was carried out under the same conditions as those of Example 3, except that phenylboronic acid was replaced with 4-biphenylboronic acid, whereby a white powder of biphenyl-4-yl-(4-phenanthrene-9-yl-phenyl)-[1,1';4',1";2",1'":4'",1""]quinquephenyl-4"-yl-amine (1-12): 8.0 g (yield: 73%) was obtained.

[Chemical Formula 11]

(1-12)

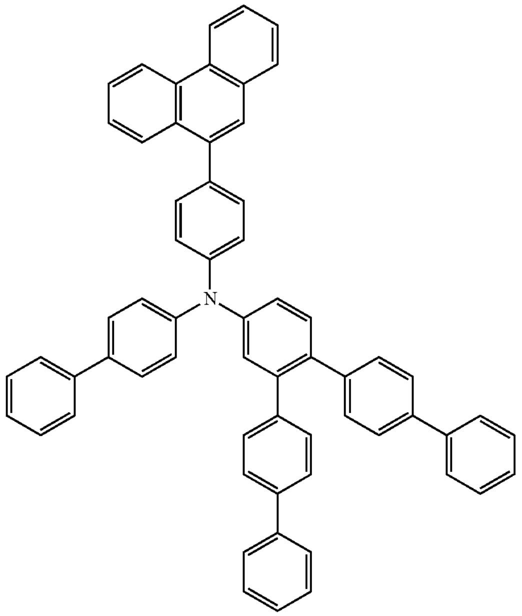

The structure of the obtained white powder was identified by NMR.

$^1$H-NMR ($CDCl_3$) detected 43 hydrogen signals, as follows. δ(ppm)=8.76-8.84 (2H), 8.12-8.14 (1H), 7.94-7.96 (1H), 7.79 (1H), 7.60-7.75 (12H), 7.42-7.56 (18H), 7.28-7.39 (8H).

Example 8

Synthesis of phenyl-(4-phenanthrene-9-yl-phenyl)-(4-naphthalen-1-yl-[1,1';2',1"]terphenyl-4'-yl)-amine (1-23)

(4-phenanthrene-9-yl-phenyl)-(4-naphthalene-1-yl-[1,1';2',1"]terphenyl-4'-yl)-amine: 13.3 g, bromobenzene: 3.7 g, tert-butoxy sodium: 3.1 g, and toluene: 130 mL were added into a reaction vessel, and the mixture was aerated with nitrogen gas under ultrasonic irradiation for 30 minutes. Then, palladium(II) acetate: 0.1 g, tri(tert-butyl)phosphine: 0.2 g were added thereto, and the mixture was refluxed and stirred for 22 hours. After allowing to cool, the filtrate obtained by filtration was concentrated under reduced pressure to obtain a crude product. The crude product was purified by recrystallizing with a toluene solvent and acetone solvent, whereby a white powder of phenyl-(4-phenanthrene-9-yl-phenyl)-(4-naphthalen-1-yl-[1,1';2',1"]terphenyl-4'-yl)-amine (1-23): 11.5 g (yield: 77%) was obtained.

[Chemical Formula 12]

(1-23)

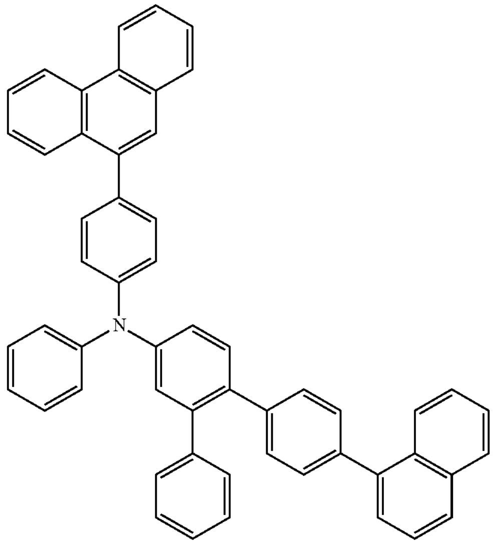

The structure of the obtained white powder was identified by NMR.

$^1$H-NMR ($CDCl_3$) detected 37 hydrogen signals, as follows. δ(ppm)=8.75-8.84 (2H), 8.12-8.18 (1H), 7.86-7.98 (4H), 7.12-7.73 (30H).

Example 9

Synthesis of phenyl-(4-phenanthrene-9-yl-phenyl)-(4-naphthalen-2-yl-[1,1';2',1"]terphenyl-4'-yl)-amine (1-24)

The reaction was carried out under the same conditions as those of Example 8, except that (4-phenanthrene-9-yl-phenyl)-(4-naphthalene-1-yl-[1,1';2',1"]terphenyl-4'-yl)-amine was replaced with (4-phenanthrene-9-yl-phenyl)-(4-naphthalene-2-yl-[1,1';2',1"]terphenyl-4'-yl)-amine, whereby a white powder of phenyl-(4-phenanthrene-9-yl-phenyl)-(4-naphthalen-2-yl-[1,1';2',1"]terphenyl-4'-yl)-amine (1-24): 9.3 g (yield: 73%) was obtained.

[Chemical Formula 13]

(1-24)

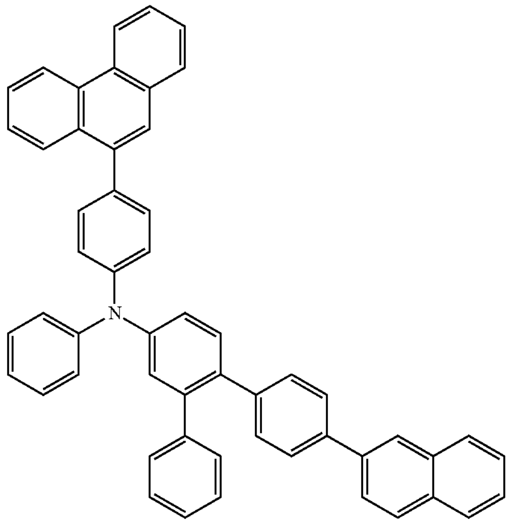

The structure of the obtained white powder was identified by NMR.

$^1$H-NMR ($CDCl_3$) detected 37 hydrogen signals, as follows. δ(ppm)=8.75-8.83 (2H), 8.08-8.12 (2H), 7.88-7.95 (4H), 7.62-7.79 (8H), 7.23-7.54 (20H), 7.14-7.16 (1H).

Example 10

Synthesis of naphthalene-1-yl-(4-phenanthrene-9-yl-phenyl)-[1,1';2',1",4",1'"]quarterphenyl-5'-yl-amine (1-29)

(4-phenanthrene-9-yl-phenyl)-[1,1';2',1",4",1'"]quarterphenyl-5'-yl-amine: 20.0 g, 1-bromonaphthrene: 8.0 g, tert-butoxy sodium: 5.0 g, toluene: 200 mL were added into a reaction vessel, and the mixture was aerated with nitrogen gas under ultrasonic irradiation for 30 minutes. Then, palladium(II) acetate: 0.4 g, tri(tert-butyl)phosphine: 0.7 g were added thereto, and the mixture was refluxed and stirred for 2 hours. After allowing to cool, the filtrate obtained by filtration was concentrated under reduced pressure to obtain a crude product. The crude product was purified by recrystallizing with a toluene solvent and acetone solvent, whereby a white powder of naphthalene-1-yl-(4-phenanthrene-9-yl-phenyl)-[1,1';2',1",4",1'"]quarterphenyl-5'-yl-amine (1-29): 4.4 g (yield: 18%) was obtained.

[Chemical Formula 14]

(1-29)

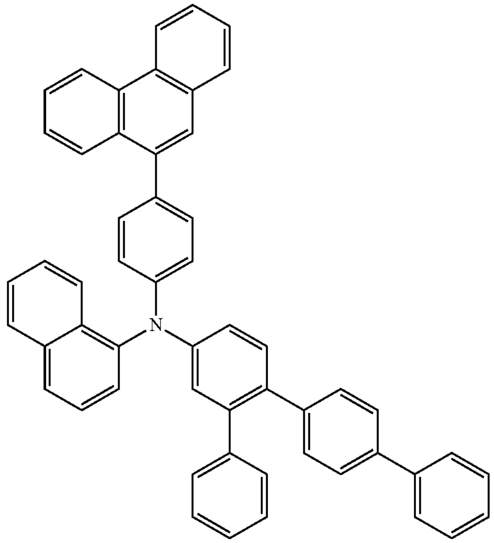

The structure of the obtained white powder was identified by NMR.

$^1$H-NMR ($CDCl_3$) detected 37 hydrogen signals, as follows. δ(ppm)=8.73-8.81 (2H), 8.17-8.20 (1H), 8.07-8.09 (1H), 7.97-8.01 (1H), 7.86-7.91 (2H), 7.29-7.74 (22H), 7.14-7.24 (8H).

Example 11

Synthesis of biphenyl-4-yl-(4-phenanthrene-9-yl-phenyl)-[1,1';3',1";2",1'":4'",1""]quinquephenyl-4"-yl-amine (1-41)

The reaction was carried out under the same conditions as those of Example 3, except that phenylboronic acid was replaced with 3-biphenylboronic acid, whereby a white powder of biphenyl-4-yl-(4-phenanthrene-9-yl-phenyl)-[1,1';3',1";2",1'":4'",1""]quinquephenyl-4"-yl-amine (1-41): 5.6 g (yield: 51%) was obtained.

[Chemical Formula 15]

(1-41)

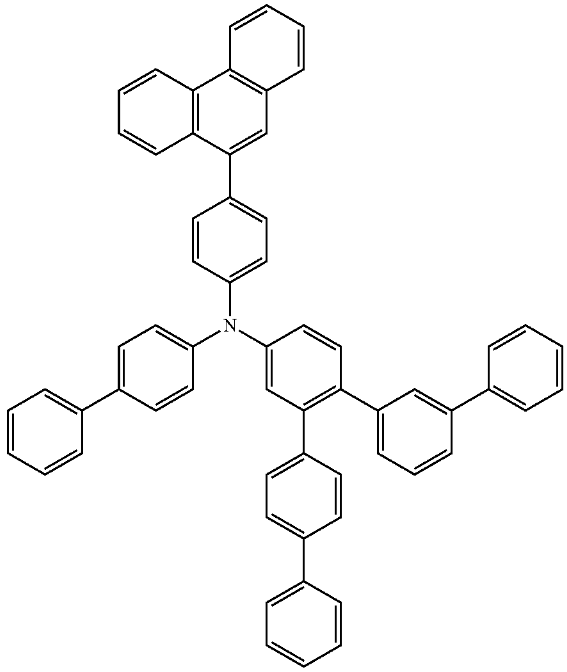

The structure of the obtained white powder was identified by NMR.

$^1$H-NMR ($CDCl_3$) detected 43 hydrogen signals, as follows. δ(ppm)=8.75-8.84 (2H), 8.12-8.14 (1H), 7.94-7.96 (1H), 7.79 (1H), 7.60-7.75 (10H), 7.27-7.56 (28H).

Example 12

Synthesis of [1,1':3',1"]terphenyl-4-yl-(4-phenanthrene-9-yl-phenyl)-[1,1';2',1"]terphenyl-4'-yl-amine (1-60)

(4-phenanthrene-9-yl-phenyl)-[1,1';2',1"]terphenyl-4'-yl-amine: 9.2 g, 4-bromo-[1,1':3',1"]terphenyl:5.2 g, tert-butoxy sodium: 1.9 g, toluene: 78 mL were added into a reaction vessel, and the mixture was aerated with nitrogen gas under ultrasonic irradiation for 30 minutes. Then, palladium (II) acetate; 0.1 g, tri(tert-butyl)phosphine; 0.1 g were added thereto, and the mixture was refluxed and stirred for 3 hours. After allowing to cool, the filtrate obtained by filtration was concentrated to obtain a crude product. The crude product was purified using column chromatography, whereby a white powder of [1,1':3',1"]terphenyl-4-yl-(4-phenanthrene-9-yl-phenyl)-[1,1';2',1"]terphenyl-4'-yl-amine (1-60); 7.1 g (yield: 58%) was obtained.

[Chemical Formula 16]

(1-60)

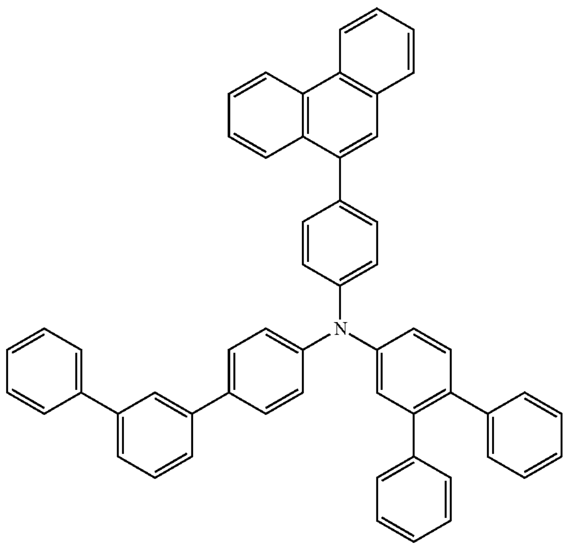

The structure of the obtained white powder was identified by NMR.

$^1$H-NMR ($CDCl_3$) detected 39 hydrogen signals, as follows. δ(ppm)=8.75-8.84 (2H), 8.11-8.13 (1H), 7.93-7.95 (1H), 7.87 (1H), 7.78 (1H), 7.48-7.72 (15H), 7.17-7.43 (18H).

Example 13

Synthesis of [1,1':4',1"]terphenyl-4-yl-(4-phenanthrene-9-yl-phenyl)-[1,1';2',1":3",1'"]quarterphenyl-5'-yl-amine (1-61)

(4-phenanthrene-9-yl-phenyl)-[1,1';2',1":3",1'"]quarterphenyl-5'-yl-amine: 8.9 g, 4-bromo-[1,1':4',1"]terphenyl: 4.0 g, tert-butoxy sodium: 1.9 g, toluene: 40 mL were added into a reaction vessel, and the mixture was aerated with nitrogen gas under ultrasonic irradiation for 30 minutes. Then, palladium(II) acetate; 0.1 g, tri(tert-butyl)phosphine; 0.2 g were added thereto, and the mixture was refluxed and stirred for 5 hours. After allowing to cool, the filtrate obtained by filtration was concentrated to obtain a crude product. The crude product was purified by crystallization with a mixed solvent of toluene/acetone, whereby a white powder of [1,1':4',1"]terphenyl-4-yl-(4-phenanthrene-9-yl-phenyl)-[1,1';2',1":3",1'"]quarterphenyl-5'-yl-amine (1-61); 9.1 g (yield: 88%) was obtained.

[Chemical Formula 17]

(1-61)

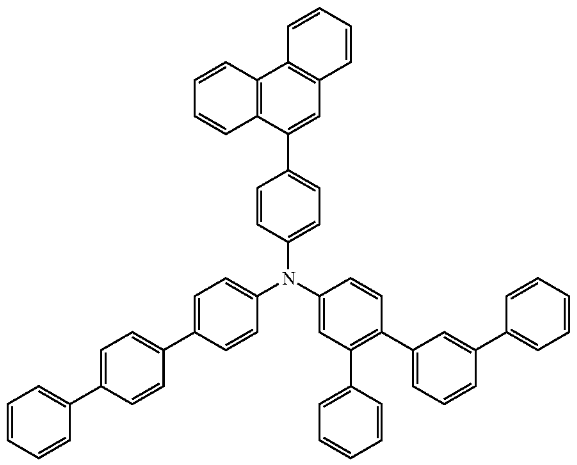

The structure of the obtained white powder was identified by NMR.

$^1$H-NMR ($CDCl_3$) detected 43 hydrogen signals, as follows. δ(ppm)=8.76-8.84 (2H), 8.11-8.13 (1H), 7.94-7.96 (1H), 7.79 (1H), 7.61-7.75 (12H), 7.22-7.56 (26H).

Example 14

Synthesis of compound (2-11)

1-bromobenzene (D-substituted): 45.0 g, 4-tert-butylaniline: 58.0 g, palladium (II) acetate: 1.0 g, tert-butoxy sodium: 30.0 g, bis(diphenylphosphino)-1,1'-binaphthyl: 2.0 g, toluene: 450 mL were added into a reaction vessel, and the mixture was refluxed and stirred for 24 hours. After allowing to cool, the mixture was concentrated and purified using column chromatography, whereby a powder of the following compound (2-11a): 49.9 g (yield: 78%) was obtained.

[Chemical Formula 18]

(2-11a)

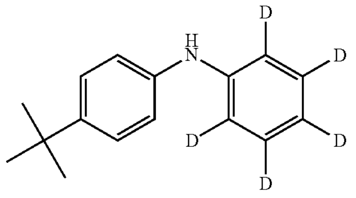

The above compound (2-11a): 20.0 g, the following compound (2-11b): 18.4 g, palladium (II) acetate: 0.5 g, tert-butyl sodium: 18.9 g, tri(tert-butyl)phosphine: 0.8 g, toluene: 200 mL were added into a reaction vessel, and the mixture was refluxed and stirred for 24 hours. After allowing to cool, the mixture was concentrated and purified using column chromatography, whereby a powder of the following compound (2-11c): 21.5 g (yield: 84%) was obtained.

[Chemical Formula 19]

(2-11b)

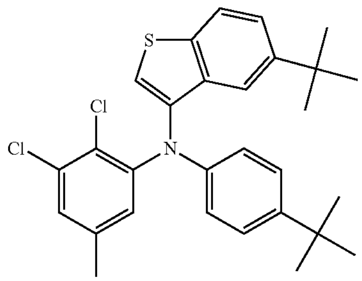

[Chemical Formula 20]

(2-11c)

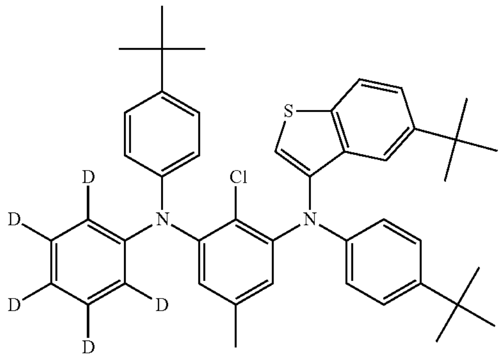

The above compound (2-11c): 12.0 g, and tert-butylbenzene: 120 mL were added into a reaction vessel. Then, 42.5 mL of n-butyllithium was added thereto dropwise at −78° C., and the mixture was aerated with nitrogen gas stirring at 60° C. for 3 hours. Then, 11.3 g of boron tribromid was added thereto dropwise at −78° C., and the mixture was stirred at room temperature for 1 hour. Then, 5.9 g of N, N-diisopropylethylamine was added thereto dropwise at 0° C., and the mixture was stirred at 120° C. for 2 hours. After allowing to cool, an aqueous sodium acetate solution was added thereto, and the mixture is stirred. An organic layer was separated and extracted with ethyl acetate, and the organic layer was concentrated. The mixture was purified using column chromatography, whereby a powder of the following compound (2-11): 1.7 g (yield: 11%) was obtained.

[Chemical Formula 21]

(2-11)

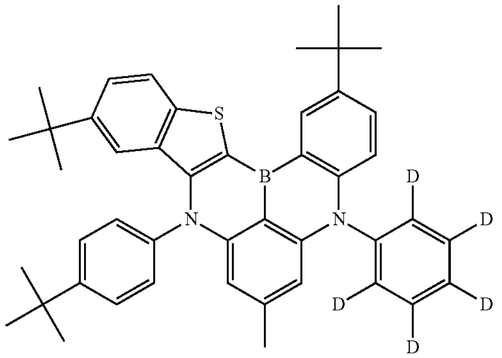

Example 15

The glass transition points (Tg) of the arylamine compounds of the general formula (1) were determined using a high-sensitive differential scanning calorimeter (DSC3100SA produced by Bruker AXS).

| Glass transition point (Tg) | |
|---|---|
| Compound of Example 1 | 118.2° C. |
| Compound of Example 2 | 118.8° C. |
| Compound of Example 3 | 127.9° C. |
| Compound of Example 4 | 129.6° C. |
| Compound of Example 5 | 134.9° C. |
| Compound of Example 6 | 125.9° C. |
| Compound of Example 7 | 139.4° C. |
| Compound of Example 8 | 117.3° C. |
| Compound of Example 9 | 119.5° C. |
| Compound of Example 10 | 132.5° C. |
| Compound of Example 11 | 126.5° C. |
| Compound of Example 12 | 110.9° C. |
| Compound of Example 13 | 123.1° C. |

The arylamine compounds of the general formula (1) have glass transition points (Tg) of 100° C. or higher, demonstrating that the compounds have a stable thin-film state.

Example 16

A 100 nm-thick vapor-deposited film was fabricated on an ITO substrate using the arylamine compounds of the general formula (1), and a work function was measured using an ionization potential measuring device (PYS-202 produced by Sumitomo Heavy Industries, Ltd.).

| Work function | |
|---|---|
| Compound of Example 1 | 5.70 eV |
| Compound of Example 2 | 5.73 eV |
| Compound of Example 3 | 5.74 eV |
| Compound of Example 4 | 5.74 eV |
| Compound of Example 5 | 5.74 eV |
| Compound of Example 6 | 5.73 eV |
| Compound of Example 7 | 5.74 eV |
| Compound of Example 8 | 5.77 eV |
| Compound of Example 9 | 5.77 eV |
| Compound of Example 10 | 5.77 eV |
| Compound of Example 11 | 5.73 eV |
| Compound of Example 12 | 5.73 eV |
| Compound of Example 13 | 5.71 eV |

As the results show, the arylamine compounds of the general formula (1) have desirable energy levels compared to the work function 5.4 eV of common hole transport materials such as NPD and TPD, and thus possess desirable hole transportability and an excellent electron blocking ability.

Example 17

Figure 10:
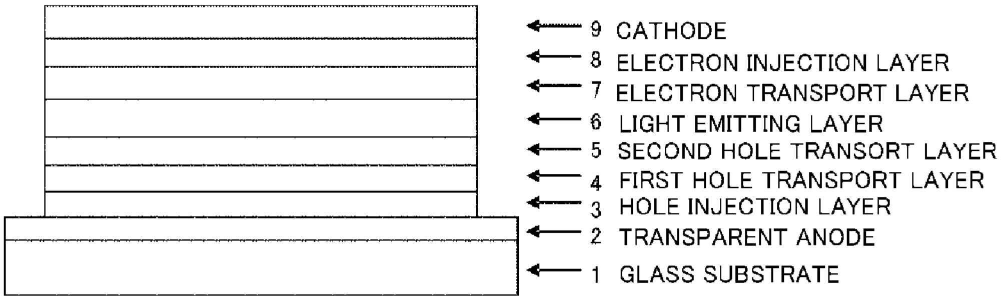
FIG. 10 is a diagram illustrating the configuration of the organic EL devices of Examples 17 to 29 and Comparative Examples 1 to 3.

The organic EL device, as shown in FIG. 10, was fabricated by vapor-depositing a hole injection layer 3, a first hole transport layer 4, a second hole transport layer 5, a light emitting layer 6, an electron transport layer 7, an electron injection layer 8, and a cathode (aluminum electrode) 9 in this order on a glass substrate 1 on which an ITO electrode was formed as a transparent anode 2 beforehand.

Specifically, the glass substrate 1 having ITO (film thickness of 150 nm) formed thereon was subjected to ultrasonic washing in isopropyl alcohol for 20 minutes and then dried for 10 minutes on a hot plate heated to 200° C. After UV ozone treatment for 15 minutes, the glass substrate with ITO was installed in a vacuum vapor deposition apparatus, and the pressure was reduced to 0.001 Pa or lower. Subsequently, as the hole injection layer 3 covering the transparent anode 2, an electron acceptor (Acceptor-1) of the structural formula below and compound (HTM-1) of the structural formula below were formed in a film thickness of 10 nm by dual vapor deposition at a vapor deposition rate ratio of Acceptor-1:compound (HTM-1)=3:97. The first hole transport layer 4 was formed on the hole injection layer 3 by forming the compounds (HTM-1) of the structural formula below in a film thickness of 55 nm. The second hole transport layer 5 was formed on the first hole transport layer 4 by forming the compound (1-2) of Example 1 in a film thickness of 5 nm. Then, the light emitting layer 6 was formed on the second hole transport layer 5 in a film thickness of 20 nm by dual vapor deposition of the compound (2-11) of Example 14 and Compound (EMH-1) of the structural formula below at a vapor deposition rate ratio of the compound (2-11):Compound (EMH-1)=5:95. The electron transport layer 7 was formed on the light emitting layer 6 in a film thickness of 30 nm by dual vapor deposition of the compound (ETM-1) of the structural formula below and Compound (ETM-2) of the structural formula below at a vapor deposition rate ratio of the compound (HTM-1): Compound (ETM-2)=50:50. The electron injection layer 8 was formed on the electron transport layer 7 by forming lithium fluoride in a film thickness of 1 nm. Finally, the cathode 9 was formed by vapor-depositing aluminum in a thickness of 100 nm. The characteristics of the thus fabricated organic EL device were measured in the atmosphere at an ordinary temperature. Table 1 summarizes the results of emission characteristics measurements performed by applying a DC voltage to the fabricated organic EL device.

[Chemical Formula 22]

(Acceptor-1)

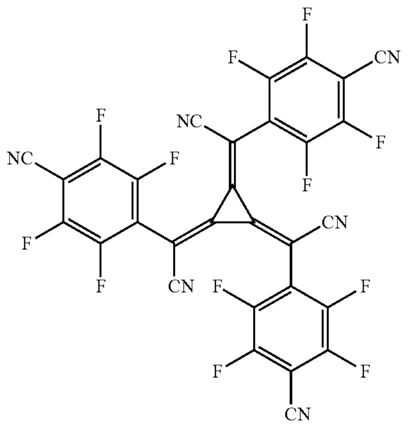

-continued
[Chemical Formula 23]
(HTM-1)
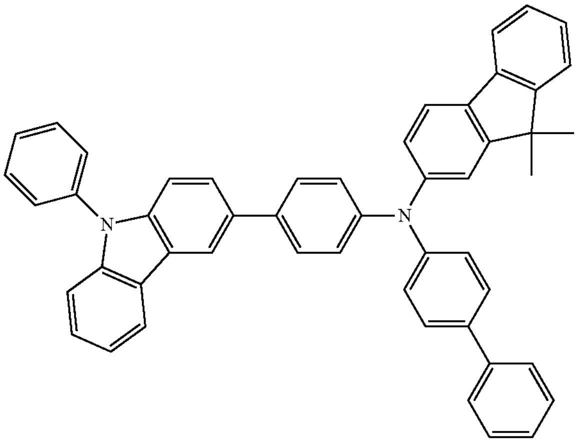
[Chemical Formula 24]
(1-2)
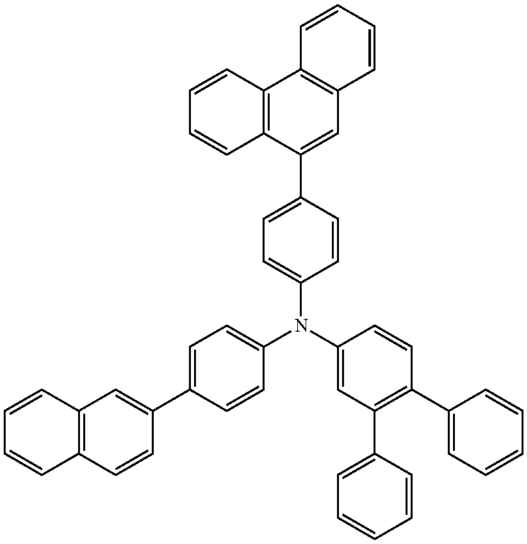
[Chemical Formula 25]
(2-11)
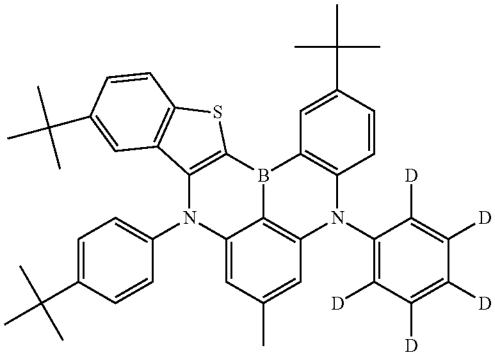
-continued
[Chemical Formula 26]
(EMH-1)
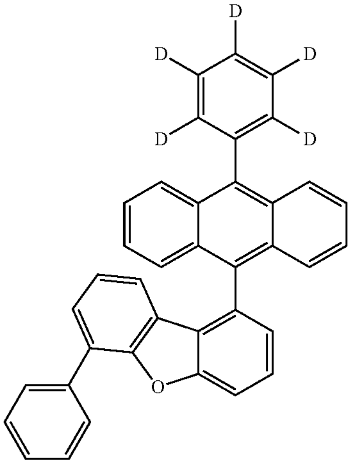
[Chemical Formula 27]
(ETM-1)
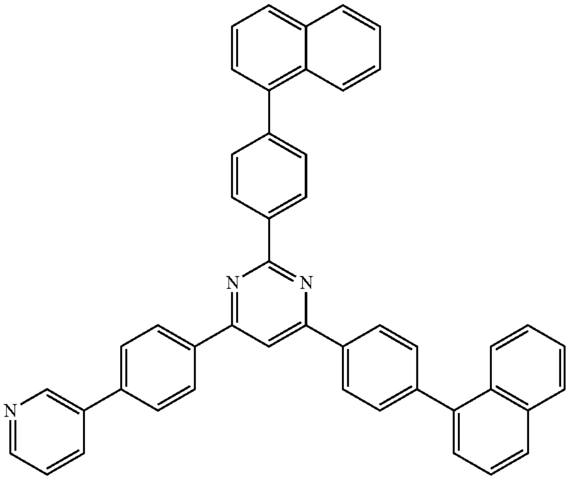
[Chemical Formula 28]
(ETM-1)
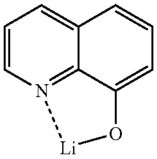

-continued

[Chemical Formula 35]

(1-23)

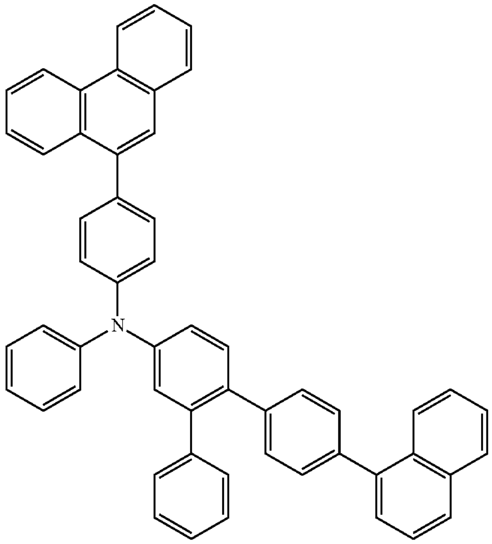

Example 18

An organic EL device was fabricated under the same conditions used in Example 17, except that the second hole transport layer 5 was formed by forming the compound (1-3) of Example 2, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 29]

(1-3)

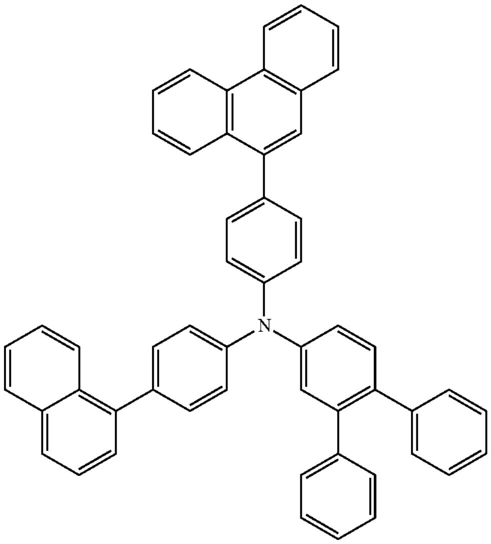

Example 19

An organic EL device was fabricated under the same conditions used in Example 17, except that the second hole transport layer 5 was formed by forming the compound (1-4) of Example 3, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 30]

(1-4)

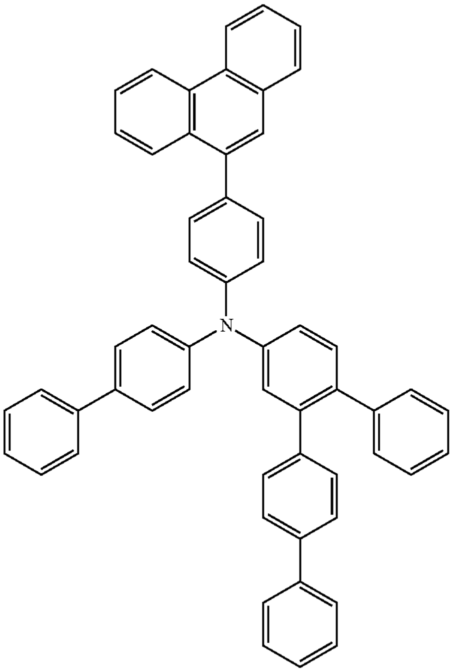

Example 20

An organic EL device was fabricated under the same conditions used in Example 17, except that the second hole transport layer 5 was formed by forming the compound (1-5) of Example 4, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 31]

(1-5)

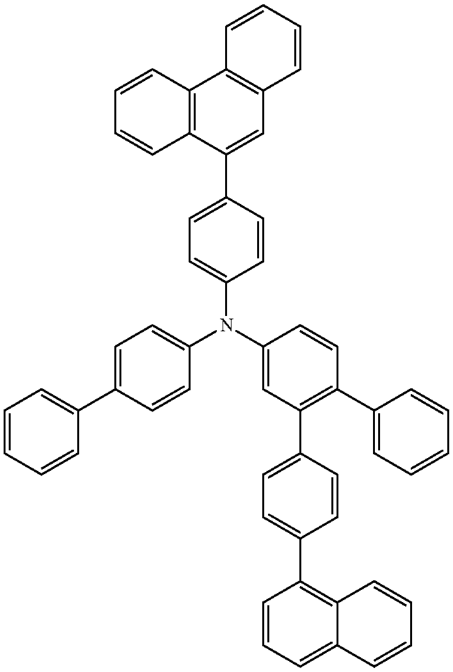

Example 21

An organic EL device was fabricated under the same conditions used in Example 17, except that the second hole transport layer 5 was formed by forming the compound (1-6) of Example 5, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 32]

(1-6)

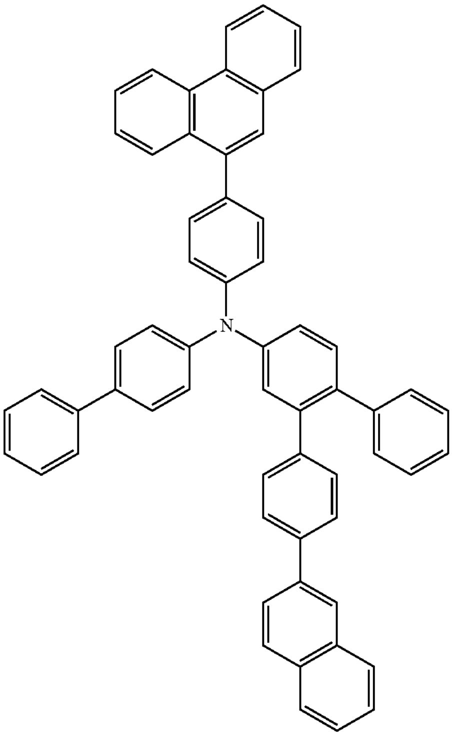

Example 22

An organic EL device was fabricated under the same conditions used in Example 17, except that the second hole transport layer 5 was formed by forming the compound (1-7) of Example 6, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 33]

(1-7)

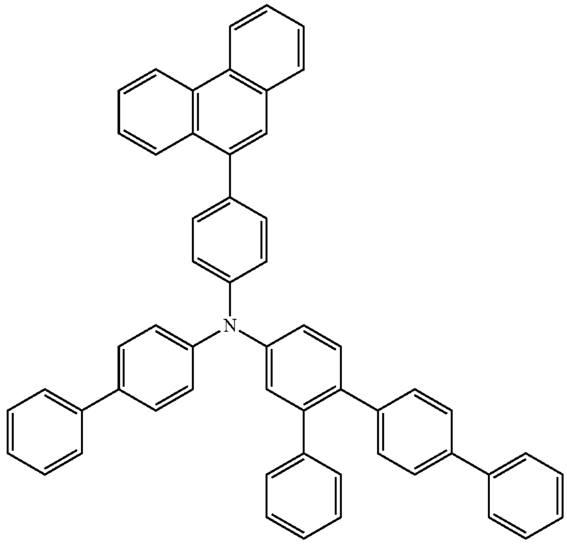

Example 23

An organic EL device was fabricated under the same conditions used in Example 17, except that the second hole transport layer 5 was formed by forming the compound (1-12) of Example 7, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 34]

(1-12)

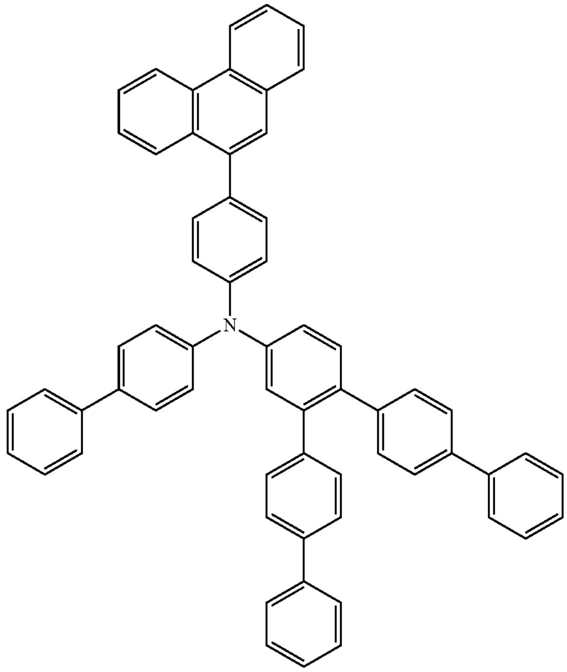

Example 24

An organic EL device was fabricated under the same conditions used in Example 17, except that the second hole transport layer 5 was formed by forming the compound (1-23) of Example 8, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 35]

(1-23)

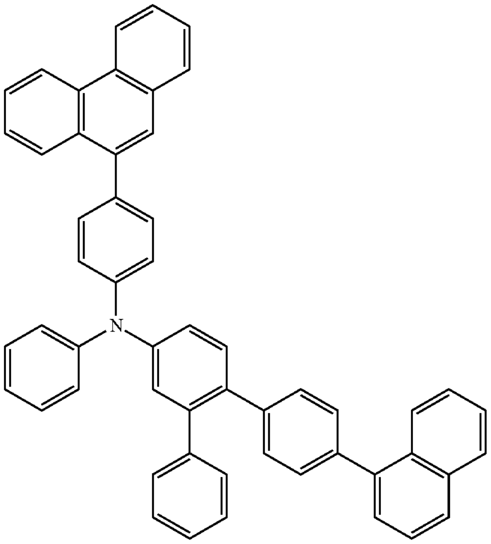

Example 25

An organic EL device was fabricated under the same conditions used in Example 17, except that the second hole transport layer 5 was formed by forming the compound (1-24) of Example 9, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 36]

(1-24)

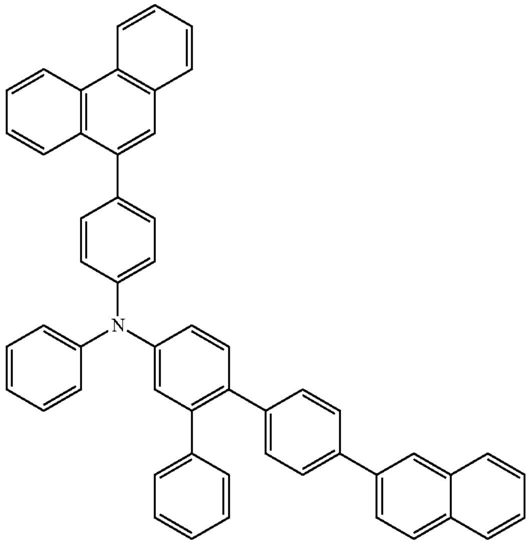

Example 26

An organic EL device was fabricated under the same conditions used in Example 17, except that the second hole transport layer 5 was formed by forming the compound (1-29) of Example 10, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 37]

(1-29)

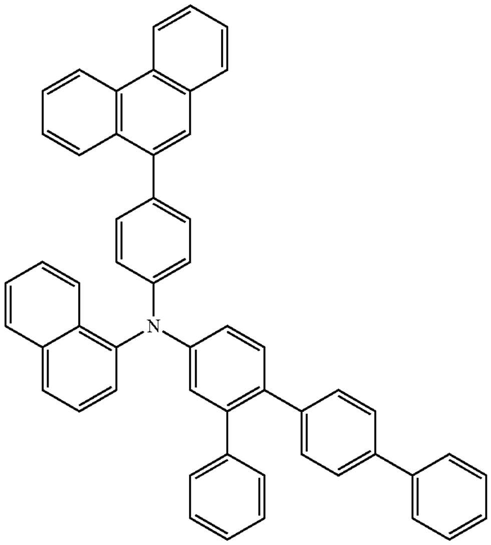

Example 27

An organic EL device was fabricated under the same conditions used in Example 17, except that the second hole transport layer 5 was formed by forming the compound (1-41) of Example 11, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 38]

(1-41)

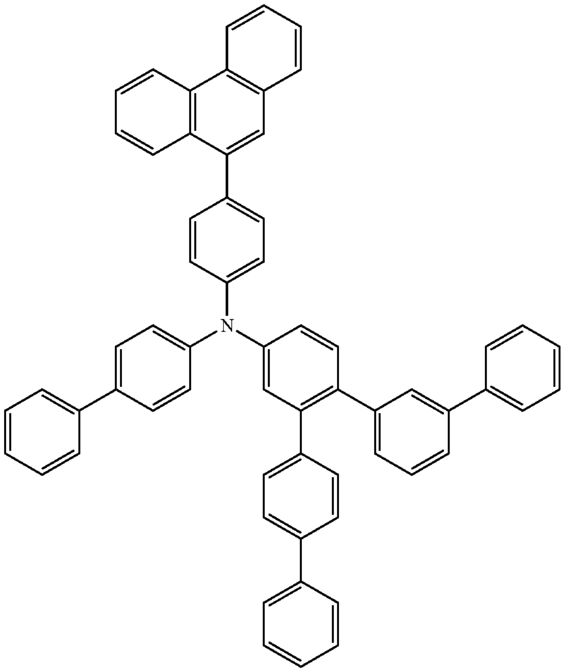

Example 28

An organic EL device was fabricated under the same conditions used in Example 17, except that the second hole transport layer 5 was formed by forming the compound (1-60) of Example 12, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 39]

(1-60)

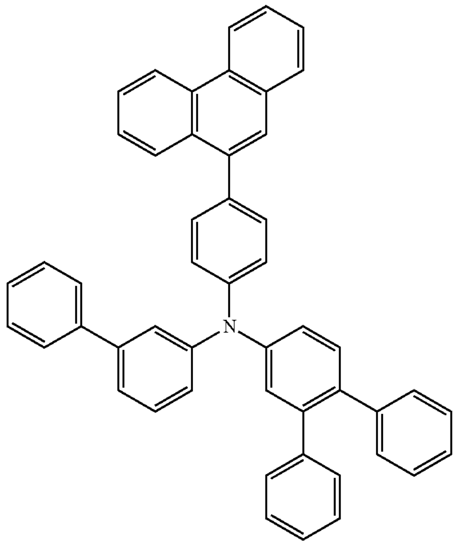

Example 29

An organic EL device was fabricated under the same conditions used in Example 17, except that the second hole transport layer 5 was formed by forming the compound (1-61) of Example 13, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 40]

(1-61)

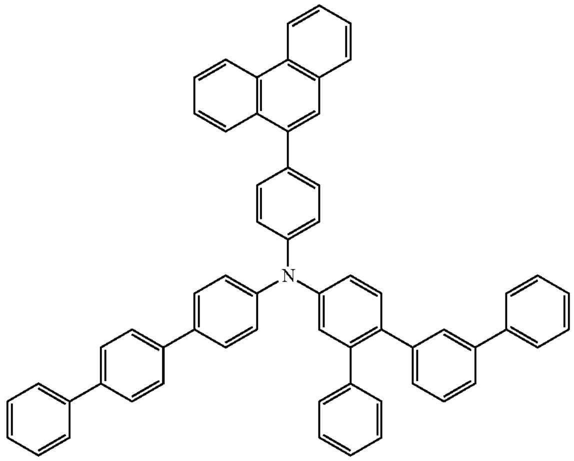

Comparative Example 1

For comparison, an organic EL device was fabricated under the same conditions used in Example 17, except that the second hole transport layer 5 was formed by forming a compound (HTM-2) of the structural formula below, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 41]

(HTM-2)

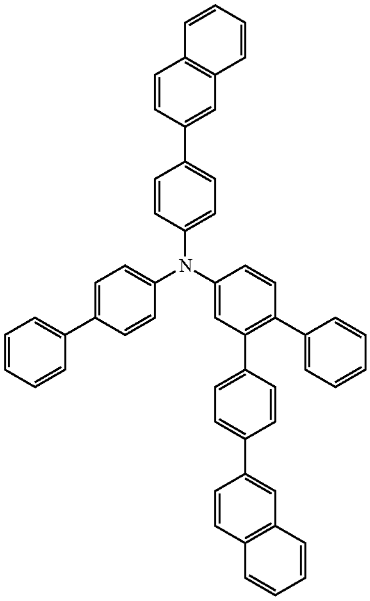

Comparative Example 2

For comparison, an organic EL device was fabricated under the same conditions used in Example 17, except that the second hole transport layer 5 was formed by forming a compound (HTM-3) of the structural formula below, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 42]

(HTM-3)

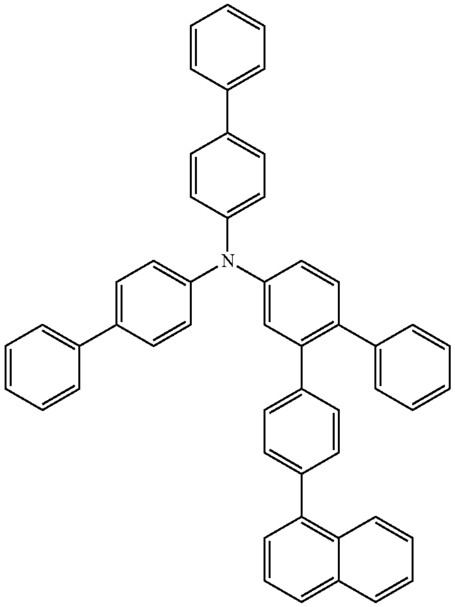

Comparative Example 3

For comparison, an organic EL device was fabricated under the same conditions used in Example 17, except that the second hole transport layer 5 was formed by forming a compound (HTM-4) of the structural formula below, instead of using the compound (1-2) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 43]

(HTM-4)

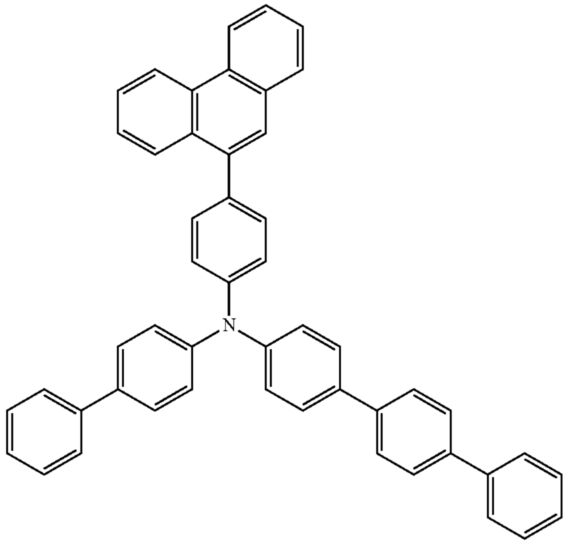

Table 1 summarizes the results of the device lifetime measurements performed with the organic EL devices fabricated in Examples 42 to 51 and Comparative Examples 1 to 4. A device lifetime was measured as the time elapsed until the emission luminance of 2,000 cd/$m^2$ (initial luminance) at the start of emission was attenuated to 1,900 cd/$m^2$ (corresponding to attenuation to 95% when taking the initial luminance as 100%) when carrying out constant current driving.

TABLE 1

| | Second hole transport layer | Voltage [V] (@10 mA/cm2) | Luminance [cd/m2] (@10 mA/cm2) | Current efficiency [cd/A] (@10 mA/cm2) | Power efficiency [lm/W] (@10 mA/cm2) | Device lifetime (Attenuation to 95%) |
|---|---|---|---|---|---|---|
| Ex. 17 | Compound 1-2 | 3.61 | 1051 | 10.51 | 9.14 | 356 h |
| Ex. 18 | Compound 1-3 | 3.66 | 1051 | 10.51 | 8.91 | 298 h |
| Ex. 19 | Compound 1-4 | 3.60 | 1044 | 10.44 | 9.10 | 285 h |
| Ex. 20 | Compound 1-5 | 3.63 | 1056 | 10.56 | 9.14 | 306 h |
| Ex. 21 | Compound 1-6 | 3.64 | 1004 | 10.04 | 8.65 | 313 h |
| Ex. 22 | Compound 1-7 | 3.58 | 1118 | 11.18 | 9.82 | 322 h |
| Ex. 23 | Compound 1-12 | 3.59 | 1038 | 10.38 | 9.09 | 323 h |
| Ex. 24 | Compound 1-23 | 3.58 | 1116 | 11.16 | 9.79 | 290 h |
| Ex. 25 | Compound 1-24 | 3.59 | 1113 | 11.13 | 9.75 | 286 h |
| Ex. 26 | Compound 1-29 | 3.60 | 1035 | 10.35 | 9.03 | 326 h |
| Ex. 27 | Compound 1-41 | 3.58 | 1044 | 10.44 | 9.17 | 308 h |
| Ex. 28 | Compound 1-60 | 3.66 | 1077 | 10.77 | 9.24 | 332 h |
| Ex. 29 | Compound 1-61 | 3.63 | 1074 | 10.74 | 9.32 | 347 h |
| Com. Ex. 1 | HTM-2 | 3.71 | 934 | 9.34 | 7.91 | 235 h |
| Com. Ex. 2 | HTM-3 | 3.71 | 794 | 7.94 | 6.72 | 223 h |
| Com. Ex. 3 | HTM-4 | 3.72 | 742 | 7.42 | 6.26 | 206 h |

As shown in Table 1, the current efficiency upon passing a current with a current density of 10 $mA/cm^2$ was 10.04 to 11.18 cd/A for the organic EL devices in Examples 17 to 29, which was higher than 7.42 to 9.34 cd/A for the organic EL devices in Comparative Examples 1 to 3. Further, the power efficiency was 8.65 to 9.82 lm/W for the organic EL devices in Examples 17 to 29, which was higher than 6.26 to 7.91 lm/W for the organic EL devices in Comparative Examples 1 to 3. Table 1 also shows that the device lifetime (attenuation to 95%) was 285 to 356 hours for the organic EL devices in Examples 17 to 29, showing achievement of a far longer lifetime than 206 to 235 hours for the organic EL devices in Comparative Examples 1 to 3.

As is clear from the above results, it was found that the organic EL device of the Example using the material of the present invention can achieve an organic EL device having high luminous efficiency and a long lifetime compared to the organic EL devices of the Comparative example using the conventional material by using the arylamine compound having a specific structure represented by the general formula (1) has greater hole mobility, and superior electron blocking ability than conventional arylamine compounds used in Comparative Examples 1 to 3.

INDUSTRIAL APPLICABILITY

In the organic EL device of the present invention in which an arylamine compound having a specific structure are using, luminous efficiency can be improved, and also durability of the organic EL device can be improved to attain potential applications for, for example, home electric appliances and illuminations.

DESCRIPTION OF REFERENCE NUMERAL

1 Glass substrate
2 Transparent anode
3 Hole injection layer
4 First hole transport layer
5 Second hole transport layer
6 Light emitting layer
7 Electron transport layer
8 Electron injection layer
9 Cathode

The invention claimed is:

1. An organic electroluminescence device comprising at least an anode, a hole transport layer, a light emitting layer, an electron transport layer, and a cathode in this order, wherein the hole transport layer comprises an arylamine compound of the following general formula (1):

(1)

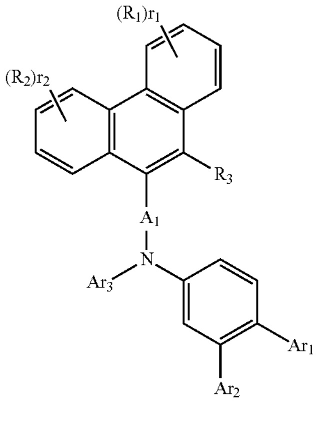

wherein $R_1$ and $R_2$ represent a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; $R_3$ represents a hydrogen atom; $A_1$ represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics; $Ar_1$ to $Ar_2$ represent a substituted or unsubstituted aromatic hydrocarbon group, a substituted or unsubstituted aromatic heterocyclic group, or a substituted or unsubstituted condensed polycyclic aromatic group; $Ar_3$ represents a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted indenyl group, a substituted or unsubstituted pyrenyl group, a substituted or unsubstituted perylenyl group, a substituted or unsubstituted fluoranthenyl group, a substituted or unsubstituted triphenylenyl group, a substituted or unsubstituted pyridyl group, a substituted or unsubstituted pyridinyl group, a substituted or unsubstituted triazinyl group, a substituted or unsubstituted furyl group, a substituted or unsubstituted pyrrolyl group, a substituted or unsubstituted thienyl group, a substituted or unsubstituted quinolyl group, a substituted or unsubstituted isoquinolyl group, a substituted or unsubstituted benzofuranyl group, a substituted or unsubstituted benzothienyl group, a substituted or unsubstituted indoyl group, a substituted or unsubstituted carbazolyl group, a substituted or unsubstituted benzooxazolyl group, a substituted or unsubstituted benzothiazolyl group, a substituted or unsubstituted quinoxalinyl group, a substituted or unsubstituted benzoimidazolyl group, a substituted or unsubstituted pyrazolyl group, a substituted or unsubstituted dibenzofuranyl group, a substituted or unsubstituted dibenzothienyl group, a substituted or unsubstituted naphthyridinyl group, a substituted or unsubstituted phenanthrolinyl, acridinyl group, or a substituted or unsubstituted carbolinyl group; $r_1$ and $r_2$ represent integers from 0 to 4; and wherein the light emitting layer includes a blue light emitting dopant, and wherein the blue light emitting dopant is a compound represented by the following general formula (2) or general formula (3):

(2)

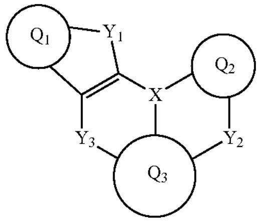

(3)

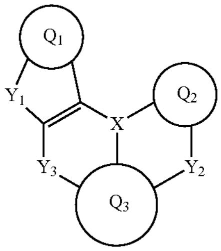

wherein, $Q_1$ to $Q_3$ may be the same or different, and represent a substituted or unsubstituted aromatic hydrocarbon, a substituted or unsubstituted condensed polycyclic aromatics, or a substituted or unsubstituted aromatic heterocyclic ring; X represents B, P, P═O, or P═S; $Y_1$ to $Y_3$ may be the same or different, and represent one of selected from N—$R_4$, $CR_5R_6$, O, S, Se and $SiR_7R_8$; $R_4$ to $R_8$ may be the same or different, and represent hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted condensed polycyclic aromatic group, or a substituted or unsubstituted aryloxy group; $R_5$ and $R_6$, and $R_7$ and $R_8$ may bind to each other to form a ring via a single bond, substituted or unsubstituted methylene, an oxygen atom, or a sulfur atom; when $Y_1$ to $Y_3$ are N—$R_4$, $CR_5R_6$, or $SiR_7R_8$, $R_4$ to $R_8$ may bind to $Q_1$, $Q_2$, or $Q_3$, which adjacent to $R_4$ to $R_8$ respectively, to form a ring via a linking group, such as substituted or unsubstituted methylene, an oxygen atom, a sulfur atom, or a monosubstituted amino group.

2. The organic electroluminescent device according to claim 1, wherein the hole transport layer has a two-layer structure of a first hole transport layer and a second hole transport layer, and the second hole transport layer includes the arylamine compound of the general formula (1).

3. The organic electroluminescent device according to claim 1, wherein the arylamine compound represented by the general formula (1) is an arylamine compound represented by the following general formula (1a):

(1a)

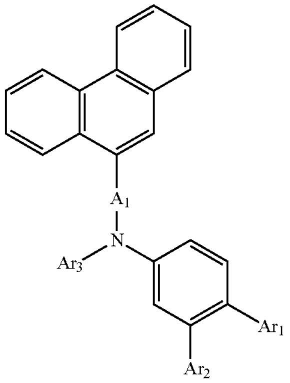

wherein $A_1$ and $Ar_1$ to $Ar_3$ are as defined by the general formula (1).

4. The organic electroluminescent device according to claim 1, wherein $Ar_3$ in the general formula (1) or the general formula (1a) represents a substituted or unsubstituted phenyl group.

5. The organic electroluminescent device according to claim 1, wherein $A_1$ in the general formula (1) or the general formula (1a) represents a divalent group that results from the removal of two hydrogen atoms from substituted or unsubstituted benzene.

6. The organic electroluminescent device according to claim 1, wherein the light emitting layer includes an anthracene derivative having an anthracene skeleton in the molecule.

7. The organic electroluminescent device according to claim 6, wherein the light emitting layer includes a host material that is an anthracene derivative having an anthracene skeleton in the molecule.

8. The organic electroluminescent device according to claim 2, wherein the arylamine compound represented by the general formula (1) is an arylamine compound represented by the following general formula (1a);

(1a)

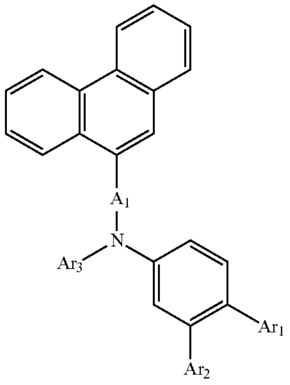

wherein $A_1$ and $Ar_1$ to $Ar_3$ are as defined by the general formula (1).

9. The organic electroluminescent device according to claim 2, wherein $Ar_3$ in the general formula (1) or the general formula (1a) represents a substituted or unsubstituted phenyl group.

10. The organic electroluminescent device according to claim 3, wherein $Ar_3$ in the general formula (1) or the general formula (1a) represents a substituted or unsubstituted phenyl group.

11. The organic electroluminescent device according to claim 2, wherein $A_1$ in the general formula (1) or the general formula (1a) represents a divalent group that results from the removal of two hydrogen atoms from substituted or unsubstituted benzene.

12. The organic electroluminescent device according to claim 3, wherein $A_1$ in the general formula (1) or the general formula (1a) represents a divalent group that results from the removal of two hydrogen atoms from substituted or unsubstituted benzene.

13. The organic electroluminescent device according to claim 4, wherein $A_1$ in the general formula (1) or the general formula (1a) represents a divalent group that results from the removal of two hydrogen atoms from substituted or unsubstituted benzene.

* * * * *